US006855829B2

(12) United States Patent
Dworetzky et al.

(10) Patent No.: US 6,855,829 B2
(45) Date of Patent: *Feb. 15, 2005

(54) 3-FLUORO-2-OXINDOLE MODULATORS OF KCNQ POTASSIUM CHANNELS AND USE THEREOF IN TREATING MIGRAINE AND MECHANISTICALLY RELATED DISEASE

(75) Inventors: Steven I. Dworetzky, Middlefield, CT (US); Valentin K. Gribkoff, Wallingford, CT (US); Gene G. Kinney, Collegeville, PA (US); Piyasena Hewawasam, Middletown, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 87 days.

This patent is subject to a terminal disclaimer.

(21) Appl. No.: 10/075,703

(22) Filed: Feb. 14, 2002

(65) Prior Publication Data

US 2002/0128277 A1 Sep. 12, 2002

Related U.S. Application Data

(60) Provisional application No. 60/269,967, filed on Feb. 20, 2001.

(51) Int. Cl.$^7$ .............................................. C07D 209/34
(52) U.S. Cl. ...................................... 548/486; 514/416
(58) Field of Search .......................... 514/418; 548/486

(56) References Cited

U.S. PATENT DOCUMENTS

| | | | | |
|---|---|---|---|---|
| 5,565,483 A | 10/1996 | Hewawasam et al. | ...... | 514/411 |
| 5,602,169 A | 2/1997 | Hewawasam et al. | ...... | 514/418 |
| 5,869,509 A | 2/1999 | Romine et al. | ............. | 514/364 |
| 6,034,113 A | 3/2000 | Hewawasam et al. | ...... | 514/364 |
| 6,117,900 A | 9/2000 | Rundfeldt et al. | .......... | 514/485 |
| 6,469,042 B1 * | 10/2002 | Hewawasam et al. | ...... | 514/411 |
| 2003/0181507 A1 * | 9/2003 | Jensen et al. | ................ | 514/411 |

FOREIGN PATENT DOCUMENTS

| | | |
|---|---|---|
| WO | WO9729748 | 8/1997 |
| WO | WO9907832 | 2/1999 |
| WO | WO0110380 A2 | 2/2001 |
| WO | WO0110381 A2 | 2/2001 |
| WO | WO0200217 A1 | 1/2002 |
| WO | WO0230868 A1 | 4/2002 |
| WO | WO02066426 A2 | 8/2002 |

OTHER PUBLICATIONS

No Author, Trilateral Project B3b Theme: Comparative study on "reach–through claims" [online]. San Francisco, California, Nov. 5–9, 2001, [retrieved on Jun. 26, 2003]. Ret'd Internet <http://www.uspto.gov/web/tws/B3b_reach-through.pdf>.*

C. Biervert et al, "A Potassium Channel Mutation in Neonatal Human Epilepsy", Science, 279:403–406 (1998).

D. D. Celentano et al., "Medication Use and Disability Among Migraineurs: A National Probability Sample Survey", Headache, 32:223–228 (1992).

C. Charlier et al., "A pore mutation in novel KQT–like potassium channel gene in an idiopathic epilepsy family", Nature Genetics, 18:53–55 (1998).

J. Edmeads et al., "Impact of Migraine and Tension–Type Headache on Life–Style, Consulting Behaviour, and Medication Use: A Canadian Population Survey", Can. J. Neurol. Sci. 20:131–137 (1993).

R. B. Lipton et al., "Undiagnosed Migraine Headaches, A Comparison of Sympton–Based and Reported Physician Diagnosis", Arch Intern Med., 152:1273–1278 (1992).

R. B. Lipton and W. F. Stewart, "Migraine in the United States: A review of epidemiology and health care use", Neurology, 43(suppl3):S6–S10 (1993).

R. B. Lipton and W. F. Stewart, "Medical Consultation for Migraine", Neurology [abstract], 44(suppl2):199 (1994).

B. K. Rasmussen et al., "Impact of headache on sickness absence and utilization of medical services: a Danish population study", J Epidemiol Community Health, 46:443–446 (1992).

B.K. Rasmussen and N. Breslau, "Migraine: Epidemiology", The Headaches, Eds. Olesen, Tfelt–Hansen, Welch, New York, NY: Raven Press; Chptr. 22:169–173 (1993).

N. A. Singh et al., "A novel potassium channel gene, KCNQ2, is mutated in an inherited epilepsy of newborns", Nature Genetics, 18:25–29 (1998).

W. F. Stewart et al., "Prevalence of Migraine Headache in the United States, Relation ot Age, Income, Race, and Other Sociodemographic Factors", JAMA, 267:64–69 (1992).

W.F. Stewart et al., "Migraine heterogeneity, Disability, pain intensity, and attack frequency and duration", Neurology, 44(suppl 4):S24–S39 (1994).

H.–S. Wang et al., "KCNQ2 and KCNQ3 Potassium Channel Subunits: Modular Correlates of the M–Channel", Science, 282, pp. 1890–1893 (1998).

* cited by examiner

Primary Examiner—Thomas C. McKenzie
(74) Attorney, Agent, or Firm—John A. Lamerdin; Aldo A. Algieri

(57) ABSTRACT

Compounds which function as modulators, particularly, openers, of human KCNQ potassium channel proteins or polypeptides, particularly, central nervous system (CNS)-located KCNQ potassium channels, and heteromultimers thereof, and their use in the treatment of migraine are provided by the present invention. One novel type of potassium channel polypeptide openers provided by the present invention is the fluorooxindole compounds, described for the first time as therapeutics for the treatment of migraine by preventing the asynchronous firing of neurons. Other KCNQ potassium channel opener compounds that are also useful in the treatments of the invention include 2,4-disubstituted pyrimidine-5-carboxamide derivatives. One or more of the compounds according to the present invention may be utilized alone, in combination, or in conjunction with other treatment modalities for reducing, ameliorating and/or alleviating migraine or diseases similar to, or mechanistically related to, migraine, e.g., cluster headache.

8 Claims, 7 Drawing Sheets

3-FLUORO-2-OXINDOLE MODULATORS OF KCNQ POTASSIUM CHANNELS AND USE THEREOF IN TREATING MIGRAINE AND MECHANISTICALLY RELATED DISEASE

CROSS-REFERENCE TO RELATED APPLICATIONS

This is a non-provisional application which claims the benefit of U.S. Provisional Application No. 60/269,967 filed Feb. 20, 2001.

FIELD OF THE INVENTION

The present invention relates generally to the KCNQ family of potassium channels and their involvement in the treatment of migraine and associated disorders. More specifically, the present invention provides modulators of central nervous system (CNS)-related potassium channel polypeptides, e.g., KCNQ2, KCNQ3, KCNQ4, KCNQ5, or heteromultimers thereof, particularly human CNS KCNQ potassium channels, which are effective in reducing, ameliorating and treating migraine (also termed migraine headache). Preferably, the KCNQ potassium channel modulators are openers or activators of central nervous system located KCNQ potassium channel polypeptides and are useful in the treatment of neurological and neurophysiological conditions, disorders and diseases, with particular regard to migraine.

BACKGROUND OF THE INVENTION

Potassium ($K^+$) channels are membrane-spanning proteins that generally act to hyperpolarize neurons. Physiological studies indicate that potassium currents are found in most cells and are associated with a wide range of functions, including the regulation of the electrical properties of excitable cells. Depending on the type of potassium channel, its functional activity can be controlled by transmembrane voltage, different ligands, protein phosphorylation, or other second messengers.

Potassium channels are considered to be the most diverse class of ion channels and have several critical roles in cell function. This has been demonstrated in neurons where $K^+$ channels are responsible, in part, for determining cell excitability by contributing to membrane repolarization following depolarization, resting membrane potential, and regulation of neurotransmitter release. The M-current has long been described, by electrophysiology recording methods and by pharmacology, as a dominant conductance in controlling neuronal excitability. The M-current is modulated by numerous neurotransmitters (acetylcholine, substance P, LHRH, and somatostatin), which can lead to either suppression or enhancement of current.

Two major physiological roles of the M-current are to set resting membrane potential and to control spike frequency adaptation. Pharmacological activation or suppression of M-currents by small molecules could have profound effects in controlling neuronal excitability. Recently, Wang et al. (1998, *Science,* 282:1890–1893) reported that co-assembly of the KCNQ2 and KCNQ3 potassium channels underlies a native M-current in neurons.

It is known that mutations in the KCNQ2 and KCNQ3 potassium channels are linked to benign familial neonatal convulsions (BFNC), an autosomal dominant epilepsy of newborns (Charlier et al., 1998, *Nature Genetics,* 18:53–55; Biervert et al., 1998, *Science,* 279:403–406; and Singh et al., 1998, *Nature Genetics,* 18:25–29). These two channels are members of the same molecular family as is the KCNQ1 potassium channel that is responsible for long-QT syndrome in the heart. Although their exact physiological functions are not well understood, the KCNQ2 and/or KCNQ3, as well as the KCNQ4 and KCNQ5, potassium channels, which are localized within the nervous system, may act to repolarize neuronal membranes that have been depolarized by $Na^+$ and $Ca^{++}$ voltage-gated ion channels. If mutations affect the KCNQ role in repolarizing the cell membrane by removing or partially reducing the outward potassium currents, it is possible that the $Na^+$ and $Ca^{++}$ ion channels would remain open longer, thus creating hyperexcitation.

An estimated 23 to 25 million Americans—about 18% of women and 6% of men—suffer from migraine pain and migraine-related symptoms (W. F. Stewart et al., 1992, *JAMA,* 267:64–69). Attacks are common, with more than 50% of sufferers experiencing one or more episodes per month (Rasmussen, B. K. and Breslau N., Migraine: Epidemiology. In: *The Headaches,* Eds. Olesen J, Tfelt-Hansen P, Welch K M A, New York, N.Y.: Raven Press; 1993:Chptr. 22:169–173).

Migraine, a heterogeneous disorder, produces a wide spectrum of pain and associated disabilities, both within and among individual sufferers. The pain spectrum includes mild pain and no disability in approximately 5–15% of migraine attacks, moderate to severe pain and disability in approximately 60–70% of attacks, and incapacitating pain and total disability in the remaining approximately 25–35% of attacks (W. F. Stewart et al., 1994, *Neurology,* 44(suppl4):S24–S39; R. B. Lipton and W. F. Stewart, 1993, *Neurology,* 43(suppl3): S6–S10).

Population-based epidemiological studies in the United States and elsewhere, have found that most people with migraine are not currently consulting a physician for their migraine attacks, and only about one-third have ever been diagnosed by a doctor (J. Edmeads et al., 1993, *Can. J. Neurol Sci.,* 20:131–137; R. B. Lipton and W. F. Stewart, 1994, *Neurology [abstract],* 44(suppl2): 199; B. K. Rasmussen et al., 1992, *J Epidemiol Community Health,* 46:443–446; and G. Micieli, 1993, Suffering in Silence. In: *Migraine: a brighter future.* Ed. Edmeads J., Worthing: Cambridge Medical Publications, pp.1–7). The overwhelming majority (95% of men and 97% of women) of migraineurs, i.e., individuals who suffer from migraines, used medication to relieve pain, although only about 28% of the men and 40% of the women have used prescription medications (R. B. Lipton et al., 1992, *Arch Int Med.,* 152:1273–1278 and D. D. Celentano et al., 1992, *Headache,* 32:223–228).

Although the symptom pattern varies among migraine sufferers, the severity of migraine pain justifies a need for vigorous, yet safe and effective, treatments and therapies for the great majority of cases. Needed in the art are agents that can be used to combat and relieve migraine (and diseases similar to and mechanistically related to migraine, e.g., cluster headache), and even prevent the recurrence of migraine. Also needed are anti-migraine agents which are effective in the treatment of acute migraine, and provide the potential for prophylactic treatment of migraine as demonstrated by efficacy in a model of cortical spreading depression. Thus, a clear goal in the art is to discover new, safe, nontoxic and effective anti-migraine compounds for use as drugs, and in anti-migraine compositions thereof, and treatments using the compounds and/or compositions.

In general, the migraine condition, with or without aura, has a variety of characteristic features. Migraine attacks are episodic and self-limited. The duration of untreated or unsuccessfully-treated migraine attacks can be from several hours to several days (e.g., about four hours to about three days). Migraine attacks are relatively infrequent, with about seventy-five percent of migraine sufferers experiencing less than or equal to three attacks per month (W. F. Stewart et al., 1992, *JAMA*, 267:64–69; W. F. Stewart et al., 1994, *Neurology*, 44(suppl4):S24–S39; and R. B. Lipton and W. F. Stewart, 1993, *Neurology*, 43(suppl3):S6–S10). Common pain characteristics of migraines include pain in a unilateral location, with a pulsating quality. Pain is usually of moderate to severe intensity and is aggravated by routine physical activity. One or more of a cluster of symptoms is recognized to frequently accompany migraines, namely, nausea and/or vomiting, photophobia, phonophobia, and functional disability, i.e., difficulty in performing routine work-related and non-work-related tasks.

The prodrome phase of migraine, or the aura phase (when it occurs), are symptoms which are known to precede an acute migraine attack and severe migraine pain. Treatments are also needed to provide not only relief from a full-blown migraine attack, but also, symptomatic relief by reducing or alleviating the development of full-blown migraine attack. As will be appreciated by the routine practitioner, the prodrome phase of a condition of migraine typically occurs before aura and before severe or throbbing migraine pain. Frequently during prodrome, the migraine sufferer experiences mood changes, lethargy and tiredness.

It will also be appreciated that migrainous aura, which is frequently experienced by about 20% of migraine sufferers, precedes severe migraine pain and throbbing. Aura involves distinctive auditory and visual distortions, which may involve visual scotomas, or even hemianopia and speech abnormalities, that develop prior to severe migraine pain and throbbing.

In view of the serious and debilitating effects that migraine headaches impose on the sufferer, novel drugs and antimigranous agents that are capable of preventing a migraine attack before the migraine sufferer experiences intense, severe migraine pain and related discomforts would be especially advantageous in the art. In addition, new drugs and compounds that are capable of providing relief from an actual migraine attack after the prodrome and/or aura phases, and once migraine pain has developed, would clearly benefit the large number of individuals who suffer from migraine. It would be especially advantageous if new drugs and compounds were developed which could reduce, ameliorate, eliminate or prevent one, or a number of, the characteristic cluster of symptoms, namely, nausea, photophobia, phonophobia and basic functional disabilities, that are further associated with migraine and migraine pain that occur after the prodrome phase of a migraine headache. It would be a further benefit and advantage to have a remedy for the amelioration, relief, and/or removal of cluster headache discomfort and pain, for example in the form of novel agents and compounds that to treat and/or prevent the cluster headache problem.

Because migraine afflicts a large percentage of the population, there is a need to discover compounds and agents that are useful in therapeutics and treatments, and as components of pharmaceutical compositions, for reducing, ameliorating, or alleviating the pain and discomfort of migraine headache and other symptoms of migraine. There is also a need for preventative treatments to ward off migraine attacks. The present invention satisfies such needs by providing compounds that function as openers of the KCNQ family of potassium channel proteins to serve as anti-migraine agents or drugs and to comprise compositions for the treatment of migraine, as described herein.

U.S. Pat. No. 5,869,509 to J. L. Romine et al. ("the '509 patent") discloses diphenyl heterocyclic oxadiazolone derivatives and U.S. Pat. No. 6,034,113 to P. Hewawasam et al. ("the '113 patent"), discloses derivatives of 1,3,4-oxadiazolone, both of which are disclosed to be useful in the treatment of disorders that are responsive to the opening of the large conductance calcium-activated potassium channels, also called maxi-K channels. Because of their voltage and calcium dependence, maxi-K channels are distinct from KCNQ potassium channels, which are only voltage dependent. In addition, the pharmacology and kinetics of maxi-K channels versus KCNQ channels are frequently quite different, and the large conductance or maxi-K channels are responsive to the opener compounds specifically disclosed in the '509 and '113 patents. Thus, the compounds and their uses described in these patents are distinct from those of the present invention.

U.S. Pat. No. 6,117,900 to C. Rundfeldt et al. describes retigabine as an agent for use in methods of treating the symptoms of various types of neuropathologic pain. The patent does not disclose the use of novel central nervous system (CNS) KCNQ potassium channel protein opener or activator compounds to reduce hyperpolerization of neurons in the trigeminal caudal nucleus, as described herein for the amelioration or alleviation of migraine.

SUMMARY OF THE INVENTION

It is an object of the present invention to provide modulators of KCNQ potassium channel polypeptides, particularly human KCNQ potassium channel polypeptides, which are involved in reducing, ameliorating, or alleviating migraine, a migraine attack, or cluster headache. In accordance with the present invention, the KCNQ potassium channel polypeptides are preferably specific to and/or localized in the central nervous system (CNS), i.e., CNS-located KCNQ potassium channel polypeptides.

It is another object of the present invention to provide modulators specific for human KCNQ potassium channel polypeptides for use in the treatment or therapy for migraine, which is responsive to the selective opener activity of the modulators on the KCNQ potassium channels.

Yet another object of the present invention is to provide compounds that function as openers, or activators, of the KCNQ potassium channel polypeptides so as to prevent the asynchronous firing of neurons that occurs during a migraine or migraine attack, or that may be involved in the symptoms that precede a full-blown migraine attack or cluster headache.

It is another object of the present invention to provide fluorooxindole compounds as novel openers of KCNQ potassium channel polypeptides to affect and treat migraine. In accordance with the present invention, by their activity as openers of the KCNQ potassium channels as described, fluorooxindole compounds are useful alone, or in conjunction with other treatments, or anti-migraine agents, in the treatment of migraine and/or in migraine therapies to reduce, ameliorate or alleviate migraine.

It is yet another object of the present invention to provide 2,4-disubstituted pyrimidine-5-carboxamide derivative compounds, preferably, 2-(Pyrrolidin-1-yl)-4-(trifluoromethyl)-N-[[4-(trifluoromethyl)phenyl]methyl] pyrimidine-5-carboxamide, as openers of KCNQ potassium channel polypeptides to affect and treat migraine. In accordance with the present invention, by their activity as openers of the KCNQ potassium channels as described, 2,4-disubstituted pyrimidine-5-carboxamide derivative compounds are useful alone, or in conjunction with other treatments or anti-migraine agents, in the treatment of migraine and/or in migraine therapies to reduce, ameliorate or alleviate migraine.

It is another object of the present invention to provide screening methods employing central nervous system (CNS)-associated KCNQ potassium channels for detecting drugs and biological agents that interact with and/or modulate such CNS KCNQ potassium channels, so as to treat migraine. In accordance with the invention, the discovered drugs and biologicals are tested to determine if they modulate the KCNQ channels, for example, to prevent the asynchronous firing of neurons. Preferably, the screening methods will detect and identify those drugs or biological agents that are openers or activators of the KCNQ potassium channels.

Additional objects and advantages afforded by the present invention will be apparent from the detailed description hereinbelow.

DESCRIPTION OF THE FIGURES

The appended drawings of the figures are presented to further describe the invention and to assist in its understanding through clarification of its various aspects.

DETAILED DESCRIPTION OF THE INVENTION

Figure 1:
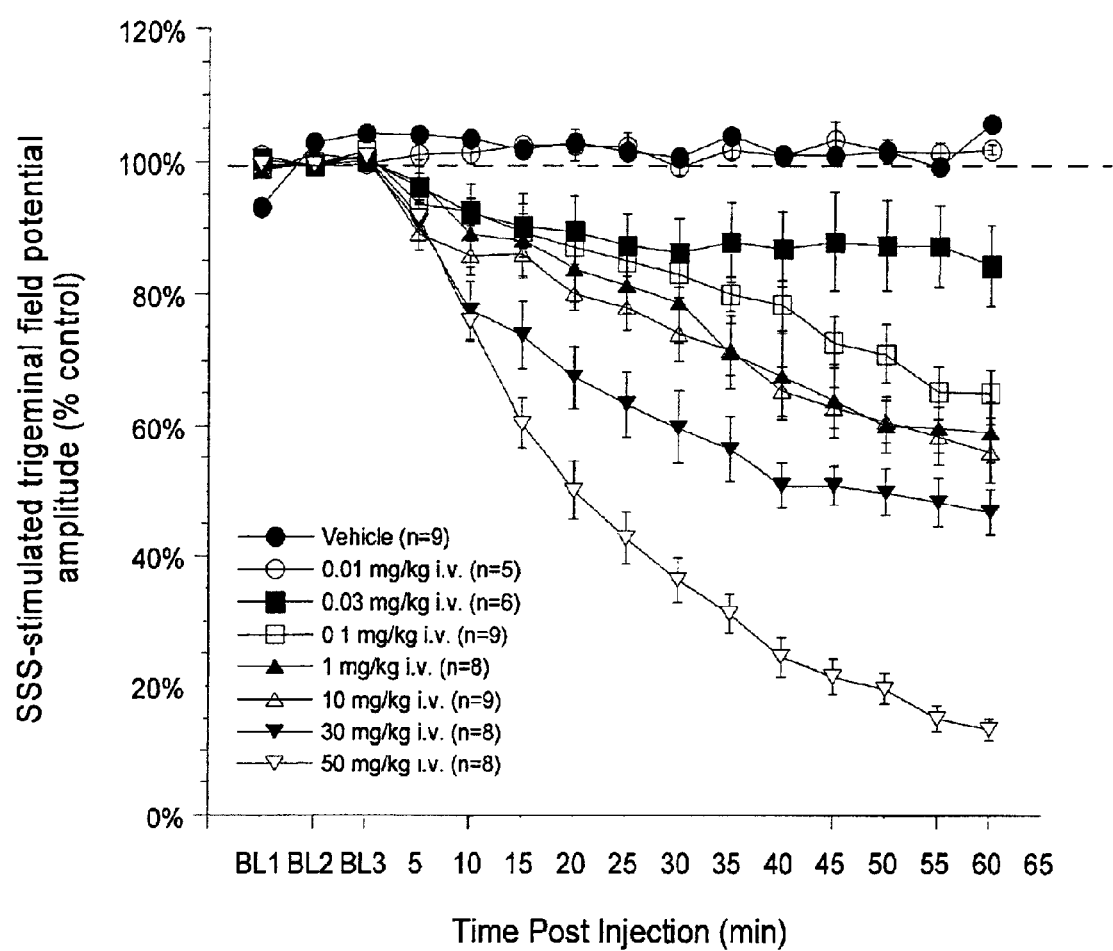
FIG. 1 depicts the effects of the representative fluorooxindole compound, (+)-3-[5-Chloro-2-[(2,2,2-trifluoroethoxy)phenyl]-1,3-dihydro-3-fluoro-6-(trifluoromethyl)-2H-indol-2-one, (Compound 1), a novel KCNQ potassium channel opener, as described herein, on SSS-stimulated field responses recorded in the nucleus trigeminal caudalis. This fluorooxindole derivative produced a significant reduction in field response following doses of 0.1–50 mg/kg i.v. (See Example 3). Error bars signify standard error of the mean (SEM).

The present invention provides modulators, preferably openers or activators, of KCNQ potassium channel proteins or polypeptides, preferably, CNS-associated human potassium channel proteins or polypeptides, which are involved in neurotransmission signaling events that occur during the onset and course of migraine headaches, or migraine attacks, as well as diseases similar to, and mechanistically related to, migraine. The term KCNQ as used herein refers to the family of KCNQ2, KCNQ3, KCNQ4 and KCNQ5 potassium channel polypeptides, and/or combinations thereof, as well as heteromultimers of different individual family members. Such heteromultimeric KCNQ potassium channel polypeptides include, but are not limited to, KCNQ2/3, KCNQ2/5 and KCNQ3/5.

The KCNQ2 and KCNQ3 potassium channel polynucleotide sequences and encoded polypeptides/proteins are described in patent application U.S. Serial No.09/105,058, filed Jun. 26, 1998; in WO 99/07832; and in WO 99/21875 A1; the KCNQ4 potassium channel protein and encoding nucleic acid sequence are described in WO 00/44786 A1; and the KCNQ5 potassium channel protein and encoding nucleic acid sequence are described in patent application U.S. Ser. No. 60/207,389, filed May 26, 2000; and in WO 00/61606 A1. The entire contents of these applications are incorporated herein by reference.

Although the exact trigger that causes a migraine is unclear, two approaches may be beneficial for treating a migrainous event. The first approach involves vasoconstriction of the vascular system and the second approach, described more fully herein, involves limiting neuronal hyperexcitability. One way to hyperpolarize neurons firing during a migraine attack is to employ selective openers, or activators, of the KCNQ potassium channels. By way of nonlimiting example, protein localization studies have demonstrated that the KCNQ2 channel is located in the trigeminal nucleus, which is a key area in migraine attacks.

Activation or opening of the KCNQ potassium channel (s), particularly the KCNQ2, or KCNQ2/3 heteromultimer, potassium channel(s), mutated or wild type, may prove to be beneficial in protection from abnormal synchronous firing during a migraine attack. The present invention provides a solution to the problem of abnormal synchronous firing of neurons related to migraine headache and diseases similar to, and mechanistically related to, migraine.

It is well documented that trigeminovascular systems are integrally involved in the transmission of migraine pain (J. W. Lance, 1993, *Mechanism and Management of Headache*, 5th edition, Butterworth Scientific, London). Specifically, neurons in the caudal region of the trigeminal nucleus caudalis are involved in this pain mediating pathway. Preclinically, it has been shown that stimulation of cerebral vasculature promotes activity in the trigeminal nucleus caudalis and produces changes in neuropeptide levels that are similar to those seen in humans during migraine (P. J. Goadsby et al., 1988, *Ann. Neurol.*, 23:193–196). Further, stimulation of these sites, in humans, produces subjective reports of pain (H. G. Wolff, 1963, Headache and Other Head Pain. Oxford University Press, New York).

Moreover, there is little doubt from a clinical standpoint that the trigeminal system is intimately involved in the expression of migraine (J. W. Lance, 1982, *Mechanisms and Management of Headache*, 4$^{th}$ Edition). The connections of the trigeminal system with cranial vessels have been termed the trigeminovascular system (TVS). More specifically, this system comprises the cranial vessels and their trigeminal innervation, implying a functional network that may play a role both in normal physiology and disease. Based on these findings, a neurogenic model of migraine has been provided, in which any stimulus which depolarizes trigeminal sensory fibers is believed to activate the TVS and induce change in the cephalic circulation and intra- and extra-cranial tissues receiving trigeminal innervation (M. A. Moskowitz, 1984, *Ann. Neurol.*, 16:157).

The mechanism by which prejunctional receptor activation leads to inhibition of neuropeptide release is unclear, and the presence of many prejunctional receptors on sensory nerves suggests that there may be a common molecular mechanism of action. Since migraine is thought to be a product of a dural vasodilation and inflammation of cranial blood vessels due to neuropeptide release, a reasonable role for a KCNQ opener is to reduce the release of vasodilating and inflammatory sensory neuropeptides from C-fibers emanating from the trigeminal ganglion.

One of the major drawbacks of most current specific abortive and/or antimigraine compounds is coronary vasoconstriction. According to the present inventors, selective neuronal inhibition within the trigeminovascular system would be a major improvement for the safety of antimigraine drugs. In one aspect of the present invention, it is demonstrated that selective KCNQ modulators, e.g., KCNQ2 and/or KCNQ3 openers or activators, are effective in modulating neuronal activity and are efficacious in the stimulated superior sagittal sinus (SSS) in vivo model of migraine and in a model of cortical spreading depression. (Example 3).

Stimulation of the superior sagittal sinus (SSS) produces a well-described physiological trigeminal response (G. A. Lambert et al., 1988, *Brain Res.*, 453:143–149), enhanced 2-deoxyglucose metabolism in cat (P. J. Goadsby and A. S. Zagami, 1991, *Brain*, 114:1001–1004) and increased c-fos immunoreactivity in the cat (H. Kaube et al., 1993b, *Brain Res.*, 629:95–102), rat (A. M. Strassman et al., 1994, *J. Neurosci.*, 14:3725–3735), and non-human primate (P. J. Goadsby and K. L. Hoskin, 1997, *J. Anat.*, 190:367–375).

Effective anti-migraine compounds with adequate brain penetration have been demonstrated to suppress SSS-stimulated trigeminal activity recorded as either single unit activity or field potentials. More specifically, compounds such as dihydroergotamine (D.H.E. 45®) (K. L. Hoskin et al., 1996, *Brain*, 119:101–108), zolmitriptan (Zomig™) (Goadsby and Hoskin, 1996 (1996, *Pain*, 67:355–359); M. J. Cumberbatch et al., 1998 (*Eur. J. Pharmacol.*, 362:43–46.)), rizatriptan (Maxalt®) (M. J. Cumberbatch et al., 1997, *Eur. J. Pharmacol.*, 328:37–40), naratriptan (Amerge™) (Y. E. Knight and P. J. Goadsby, 1997, *Cephalalgia*, 17:403 and P. J. Goadsby and Y. E. Knight, 1997, *Br. J. Pharmacol.*, 122:918–922) and, following blood-brain-barrier disruption, sumatriptan (Imitrex®) (H. Kaube et al., 1993a, *Brain Res.*, 629: 95–102) decrease physiological measures of SSS-stimulated trigeminal activity. Thus, the finding of a reduced trigeminal response following drug administration using this technique is an accepted standard with which to evaluate and compare compounds having anti-migraine potential (see M. J. Cumberbatch et al., 1999, *Br. J. Pharmacol.*, 126:1478–1486). Accordingly, the reduction of an SSS-stimulated trigeminal field potential response by a compound according to the present invention is indicative that the compound is an effective candidate for the treatment of migraine.

Cortical spreading depression (CSD) is defined as a wave of neuronal excitation, followed by long-lasting inhibition, that spreads from a focal point at a rate of 2–3 mm/min (K. S. Lashley, 1941, *Arch. Neurol. Psychiatry*, 46:331–339). It has been suggested that spreading depression may underlie various prodromes that precede the onset of migraine headache, particularly visual aura (M. Lauritzen, 1994, *Brain*, 117:199–210). Clinical neurological migraine prodromes proceed in a temporal fashion that is correlated with the expected rate of spreading depression (M. Lauritzen and J. Olesen, 1984, *Brain*, 107:447–461). These neurological symptoms are correlated with associated changes in blood flow that correlate well with the spreading depression phenomena (M. Lauritzen et al., 1983, *Ann. Neurol.*, 13:633–641). Recently, spreading depression was visualized during migraine in human subjects using functional magnetic resonance imaging based on a blood oxygenation level-dependent imaging technique (Y. Cao et al., 1999, *Arch. Neurol.*, 56:548–554).

The foregoing suggests that spreading depression may both underlie the visual aura, and possibly other prodromes, that precede migraine and cause the ensuing migraine attack and accompanying pain (J. E. Hardebo, 1991, *Headache*, 31:213–221; J. E. Hardebo, 1992, *Cephalalgia*, 12:75–80). Accordingly, attenuation of cortical spreading depression is currently accepted for evaluating and comparing novel drugs for their usefulness in the treatment, particularly prophylactic treatment, of migraine headache (see T. P. Obrenovitch and E. Zilkha, 1996, *Br. J. Pharmacol.*, 117:931–937; W. N. Chan et al., 1999, *Bioorg. Med. Chem. Lett.*, 9:285–290).

In one of its aspects, the present invention provides modulators of KCNQ potassium channel proteins or polypeptides, preferably CNS-located KCNQ potassium channel proteins or polypeptides, more preferably human CNS-located KCNQ potassium channel proteins or polypeptides, for use in modulating neuronal activity involving KCNQ potassium channel proteins or polypeptides to reduce, ameliorate, or alleviate migraine. Modulators can encompass inhibitors or antagonists, or activators or agonists or openers, of the KCNQ potassium channel proteins or polypeptides.

Preferred in the present invention are openers, or activators, of the KCNQ potassium channel proteins or polypeptides, which are responsive to the opener activity of these compounds to treat migraine, a condition which is, in turn, responsive to the opening of the KCNQ potassium channels. Especially preferred are openers or activators that are selectively active on KCNQ2, KCNQ3, and/or KCNQ2/3 potassium channel proteins or polypeptides. Human KCNQ potassium channels are most preferred. Also most preferred are KCNQ2 potassium channel proteins, particularly human KCNQ2 potassium channel proteins. The present invention particularly contemplates central nervous system located KCNQ potassium channel proteins, which are responsive to the opener or activator compounds described herein.

In an embodiment of the present invention, novel 3-fluoro-3-phenyloxindole derivatives (a.k.a., fluorooxindole compounds or 3-fluoro oxindole derivatives, herein) have been found to be effective in an in vivo model of migraine involving vasculo-trigeminal systems which are integrally involved in the transmission of migraine pain. (See Example 3). A general formula for the novel 3-fluoro oxindole derivatives which are openers or activators of the CNS KCNQ potassium channels as described herein and are suitable for use in the present invention is shown in the following general Formula I:

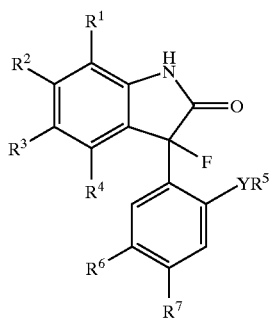

I wherein $R^1$, $R^2$, $R^3$, $R^4$, $R^5$, $R^6$, $R^7$ and Y are as defined below, or a nontoxic pharmaceutically acceptable salt, solvate or hydrate thereof More specifically with regard to Formula I, $R^1$, $R^2$, $R^3$ and $R^4$ each are independently hydrogen, $C_1$ to 4 alkyl, halogen, fluoromethyl, trifluoromethyl, phenyl, 4-methylphenyl or 4-trifluoromethylphenyl; $R^5$ is $C_1$ to 6 alkyl, optionally substituted with one to three same or different groups selected from fluoro and chloro, provided that $R^5$ is not $C_1$ to 6 alkyl when Y is O; Y is O or S; and $R^6$ and $R^7$ each are independently hydrogen, chloro, bromo or trifluoromethyl.

As used herein with respect to Formula I, the term "$C_1$ to 6 alkyl" means straight or branched chain alkyl groups such as methyl, ethyl, propyl, isopropyl, butyl, isobutyl, tert-butyl, pentyl, 4-methylbutyl, hexyl and the like. The term "$C_{1-4}$ alkyl" as used herein and in the claims means straight or branched chain alkyl groups such as methyl, ethyl, propyl, isopropyl, butyl, isobutyl, and tert-butyl. The term "halogen" as used herein is intended to include bromine, chlorine, iodine and fluorine.

As the 3-fluoro oxindole derivative compounds of the present invention possess an asymmetric carbon atom at the 3-position of the oxindole ring, the present invention contemplates the use of the racemate as well as the individual enantiomeric forms of the compounds of Formula I as described herein. Preferred embodiments of compounds of Formula I are the racemate and the single enantiomer which includes mostly the one stereoisomer having a (+) optical rotation, which is most preferred. Mixtures of isomers can be separated into individual isomers according to methods which are known to the skilled practitioner, e.g., fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns, according to procedures described herein.

Certain of the novel 3-fluoro oxindole derivatives suitable for use according to the present invention can exist in unsolvated forms as well as solvated forms including hydrated forms such as monohydrate, dihydrate, trihydrate, hemihydrate, tetrahydrate and the like. The products may be true solvates, while in other cases, the products may merely retain adventitious solvent, or be a mixture of solvate plus some adventitious solvent. It should be appreciated by those skilled in the art that solvated forms are equivalent to unsolvated forms and are intended to be encompassed within the scope of the present invention.

A representative and preferred 3-fluoro oxindole compound is (+)-3-[5-chloro-2-[(2,2,2-trifluoroethoxy)phenyl]-1,3dihydro-3-fluoro-6-(trifluoromethyl)-2H-indol-2-one, (Compound 1),which functions as a KCNQ potassium channel opener or activator according to the present invention. This compound was used in the SSS-stimulated trigeminal model for migraine as described in Example 3 herein. In addition, as seen in FIG. 1, this 3-fluoro oxindole derivative produced a dose-dependent decrease in trigeminal field potentials with the highest dose (50 mg/kg i.v.) producing a nearly complete blockade of this response (i.e., 86.7±1.67% decrease from control amplitude).

Examples of other 3-fluoro oxindole derivatives suitable for use according to the present invention include the following, as described in co-pending provisional patent application [USSN to be assigned] filed concurrently herewith and having the same assignee:

(±)-3-[5-chloro-2-[(2,2,2-trifluoroethoxy)phenyl]-1,3-dihydro-3-fluoro-6-(trifluoromethyl)-2H-indol-2-one;

(±)-3-[5-chloro-2-(2,2,2-trifluoroethoxy)phenyl]-1,3-dihydro-3,6-difluoro-2H-indol-2-one;

(±)-3-[5-chloro-2-(2,2,2-trifluoroethoxy)phenyl]-1,3-dihydro-3-fluoro-6-(fluoromethyl)-2H-indol-2-one;

(±)-3-[5-chloro-2-(2,2,2-trifluoroethoxy)phenyl]-4,6-dichloro-1,3-dihydro-3-fluoro-2H-indol-2-one;

(±)-3-[5-chloro-2-(2,2,2-trifluoroethoxy)phenyl]-5,6-dichloro-1,3-dihydro-3-fluoro-2H-indol-2-one;

(±)-3-[5-chloro-2-(2,2,2-trifluoroethoxy)phenyl]-1,3-dihydro-3,5,6-trifluoro-2H-indol-2-one;

(±)-6-chloro-3-[5-chloro-2-(2,2,2-trifluoroethoxy)phenyl]-1,3-dihydro-3-fluoro-2H-indol-2-one;

(+)-6-chloro-3-[5-chloro-2-(2,2,2-trifluoroethoxy)phenyl]-1,3-dihydro-3-fluoro-2H-indol-2-one;

(±)-3-[5-chloro-2-(2-fluoroethoxy)phenyl]-1,3-dihydro-3-fluoro-6-(trifluoromethyl)-2H-indol-2-one;

(±)-3-[4,5-dichloro-2-(2-fluoroethoxy)phenyl]-1,3-dihydro-3-fluoro-6-(trifluoromethyl)-2H-indol-2-one;

3-[5-chloro-2-(2-fluoroethylthio)phenyl]-1,3-dihydro-3-fluoro-6-(trifluoromethyl)-2H-indol-2-one;

3-[5-chloro-2-(ethylthio)phenyl]-1,3-dihydro-3-fluoro-6-(trifluoromethyl)-2H-indol-2-one;

3-[5-chloro-2-[(2-methylphenylmethyl)thio]phenyl]-1,3-dihydro-3-fluoro-6-(trifluoromethyl)-2H-indol-2-one;

3-[5-chloro-2-(2-methyl-1-propylthio)phenyl]-1,3-dihydro-3-fluoro-6-(trifluoromethyl)-2H-indol-2-one;

3-[5-chloro-2-(1-propylthio)phenyl]-1,3-dihydro-3-fluoro-6-(trifluoromethyl)-2H-indol-2-one;

3-[5-chloro-2-(2,5-difluorophenylmethylthio)phenyl]-1,3-dihydro-3-fluoro-6-(trifluoromethyl)-2H-indol-2-one;

3-[5-chloro-2-(3-chloro-1-propylthio)phenyl]-1,3-dihydro-3-fluoro-6-(trifluoromethyl)-2H-indol-2-one; and (±)-3-[5-chloro-2-(2,2,2-trifluoroethoxy)phenyl]-1,3-dihydro-3-fluoro-6-[4-(trifluoromethyl)phenyl]-2H-indol-2-one.

In another embodiment, 2,4-disubstituted pyrimidine-5-carboxamide derivatives have been found to be effective as KCNQ potassium channel openers or activators for use in the treatment of migraine according to this invention. In general, the 2,4-disubstituted pyrimidine-5-carboxamide derivative compounds have a formula as shown in II:

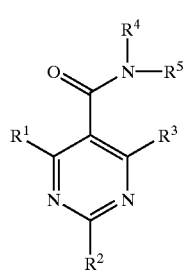

wherein,
R$^1$ is selected from hydrogen, halogen, C$_{1-8}$ alkyl, phenyl, phenylalkyl, C$_{3-6}$heterocyclic, C$_{3-6}$heterocyclicmethyl, —CN, —OR, —NRR, —NRNCOR or —CF$_3$;
R$^2$ is selected from halogen, C$_{1-8}$alkyl, C$_{3-7}$cycloalkyl, phenyl, phenylalkyl, C$_{3-6}$ heterocyclic, C$_{3-6}$heterocyclicmethyl, —CN, —OR, —NRR, —NRNCOR or —S—R; R$^3$ is selected from hydrogen, halogen or C$_{1-8}$alkyl;
R$^4$ is selected from hydrogen, —CH$_3$ or —CH$_2$C$_6$H$_5$; R$^5$ is selected from hydrogen, C$_{1-8}$alkyl, C$_{3-7}$cycloalkyl, phenyl, phenylalkyl, C$_{3-6}$heterocyclic or C$_{3-6}$ heterocyclicmethyl; and wherein each occurrence of R is independently selected from the groups consisting of C$_{1-8}$alkyl, C$_{3-7}$alkynyl, phenyl, phenylalkyl, C$_{3-6}$heterocyclic and C$_{3-6}$heterocyclicmethyl.

The terms "C$_{1-4}$ alkyl" and "C$_{1-8}$ alkyl", as used herein with respect to the compounds of Formula II, means a straight or branched chain alkyl group containing from 1 to 8 carbon atoms such as methyl, ethyl, propyl, isopropyl, butyl, sec-butyl, isobutyl, tert-butyl, pentyl, isopentyl, amyl, hexyl, isohexyl and the like. Preferably, these groups contain from 1 to 4 carbon atoms. The term "C$_{3-7}$ cycloalkyl" means a carbon cyclic ring system such as cyclopropyl, cyclobutyl, cyclopentyl, cyclohexyl and cycloheptyl. The term "C$_{3-7}$ alkynyl" means a straight or branched chain alkynyl group containing 3 to 7 carbon atoms such as 2-propyn-1-yl, 4-pentyn-1-yl, 2-butyn-1-yl, 2-methyl-3-butyn-2-yl, 3-butyn-2-yl and the like. The term "halogen" is intended to include bromo, chloro, iodo, and fluoro. The term "phenylalkyl" means a straight or branched chain C$_{1-4}$alkyl group containing an aromatic phenyl moiety such as phenylmethyl, phenylethyl, phenylbutyl and the like. The term "C$_{3-6}$heterocyclic" means a heterocyclic ring system containing from 3 to 6 carbon atoms and one or more hetero atoms such as pyrrolyl, furanyl, thienyl, imidazolyl, oxazolyl, thiazolyl, pyrazolyl, pyrrolidinyl, pyridinyl, pyrimidinyl, purinyl and the like. The general synthesis of the 2,4-disubstituted pyrimidine-5-carboxamide derivative compounds is found in co-pending provisional patent application [USSN to be assigned] filed concurrently herewith and assigned to the same assignee.

A specific example of a 2,4-disubstituted pyrimidine-5-carboxamide derivative is 2-(Pyrrolidin-1-yl)-4-(trifluoromethyl)-N-[[4-(trifluoromethyl)phenyl]methyl]pyrimidine-5-carboxamide, (Compound 2), the synthesis of which is described in Example 2 herein. 2-(Pyrrolidin-1-yl)-4-(trifluoromethyl)-N-[[4-(trifluoromethyl)phenyl]methyl]pyrimidine-5-carboxamide was shown to be an effective KCNQ2 potassium channel polypeptide opener in the treatment of migraine evaluated in the SSS-stimulated trigeminal model for migraine according to the present invention. (see Example 3 and FIG. 2).

To further investigate the effectiveness of other KCNQ potassium channel opener compounds in the methods according to the present invention, retigabine (described in DE 42 00 259) was also tested for its ability to function to treat migraine headache in the SSS-trigeminal response model, as discovered by the present inventors and as described herein. (Example 3 and FIG. 3).

In another embodiment of the present invention, one or more of the KCNQ openers as anti-migraine compounds of the present invention is included in a pharmaceutical composition, also comprising a pharmaceutically or physiologically acceptable diluent, carrier, excipient, or adjuvant, preferably for use according to the present invention. Pharmaceutical compositions suitable for use in the present invention include compositions wherein the active ingredients are contained in an effective and sufficient amount to achieve the intended purpose, either therapeutic or preventative. The determination of an effective dose is well within the capability of those skilled in the art. The therapeutically effective dose or amount can be estimated initially either in cell culture assays, e.g., of neoplastic cells, or in animal models, usually mice, rabbits, dogs, pigs, rats, monkeys, or guinea pigs. The animal model is also used to achieve a desirable concentration range and route of administration. Such information can then be used to determine useful doses and routes for administration in humans.

A therapeutically effective dose or amount refers to that amount of the KCNQ protein modulators which reduce, ameliorate, or eliminate the symptoms or condition of migraine, particularly in accordance with the present invention. A therapeutically effective amount means the total amount of each active component employed in a treatment or method that is sufficient to show a meaningful patient benefit, i.e., amelioration or healing of migraine conditions which respond to the modulation of the KCNQ potassium channels. When applied to an individual active ingredient, administered alone, the term "therapeutically effective amount" refers to that ingredient alone. When applied to a combination, the term refers to combined amounts of the active ingredients that result in the therapeutic effect, whether administered in combination, serially or simultaneously. The exact dosage is chosen by the individual physician in view of the patient to be treated, the route of administration, the severity of disease, and the like.

KCNQ-modulatory opener compounds according to the present invention may be used alone, or in combination, at appropriate dosages defined by routine testing, in order to obtain optimal modulation of a potassium channel biological activity and/or physiological condition, or its activity while minimizing any potential toxicity. Co-administration or sequential administration of other modulating agents, e.g., openers or activators, may be desirable or necessary.

The pharmaceutical compositions may be provided to an individual in need of therapeutic treatment for migraine by a variety of routes, such as subcutaneous, topical, oral, intraperitoneal, intradermal, intravenous, intranasal, bronchial, buccal, sublingual, suppository and intramuscular. Administration of pharmaceutical compositions is typically accomplished orally or parenterally. More specifically, methods of parenteral delivery include topical, intra-arterial (directly to the tissue), intramuscular, subcutaneous, intramedullary, intrathecal, intraventricular, intravenous, intraperitoneal, or intranasal administration.

The present invention also provides suitable topical, oral, systemic and parenteral pharmaceutical formulations for use in the methods of treatment for migraine comprising the KCNQ potassium channel openers or activators described herein. The compositions containing such opener/activator compounds to be utilized as the active ingredient in the treatment of migraine symptoms and/or pain can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Thus, if a solid carrier is used, the preparation may be tableted, placed in a hard gelatin capsule in powder or pellet form, or prepared in the form of a troche or lozenge. The solid carrier may contain conventional excipients, such as binding agents, fillers, tableting lubricants, disintegrants, wetting agents and the like. The tablet may, if desired or warranted, be film-coated by conventional techniques.

If a liquid carrier is employed, the preparation may be in the form of a syrup, soft emulsion, soft gelatin capsule, sterile vehicle for injection, an aqueous or non-aqueous suspension, or it may be a dry product for reconstitution with water, or another suitable vehicle, prior to use. Liquid preparations may contain conventional additives, such as suspending agents, emulsifying agents, wetting agents, non-aqueous vehicle (including edible oils), preservatives, as well as flavoring and/or coloring agents.

For parenteral administration, a vehicle will typically comprise sterile water, at least in large part, although saline solutions, glucose solutions, and the like, may be utilized. Injectable suspensions may also be used, in which case conventional suspending agents may be employed. Conventional preservatives, buffering agents, and the like, may also be added to the parenteral dosage forms. Particularly useful is the administration of the opener compounds described herein directly in parenteral formulations. The pharmaceutical compositions are prepared by conventional techniques appropriate to the desired preparation and containing appropriate amounts of the active ingredient, i.e., fluorooxindole or 2,4-disubstituted pyrimidine-5-carboxamide derivative compounds as described in accordance with the present invention. See, for example, *Remington's Pharmaceutical Sciences*, 17th edition, (Ed.) A. Osol, Mack Publishing Company, Easton, Pa., 1985.

Likewise, the modulatory KCNQ opener compounds may also be administered in intravenous (both bolus and infusion), intraperitoneal, subcutaneous, topical—with or without occlusion, or intramuscular form, all using forms well known to those of ordinary skill in the pharmaceutical arts. An effective but non-toxic amount of the compound desired can be employed as a KCNQ potassium channel modulating agent for migraine.

The dosage of the compounds according to the present invention used to achieve a desired therapeutic or preventative effect will depend not only on factors such as the age, weight, sex and condition of the patient and mode of administration, but also on the degree of KCNQ potassium channel opening activity that is desired and the potency of the particular compound being utilized in the treatment of migraine as described herein. It is contemplated, in this regard, that for the treatment of migraine, the dosage of the particular compound may be administered in unit dosage form, and that the unit dosage form will be adjusted accordingly by the skilled practitioner to reflect the relative level of activity. The decision as to the particular dosage to be employed, and the number of times a dosage will be administered per day, is within the discretion of the physician and may be varied by titration of the dosage to the particular circumstances of the present invention to produce the desired therapeutic effect.

A suitable dose of the opener compounds of the present invention, e.g., those of Formula I or II, or pharmaceutical composition thereof, for a mammal, including humans, suffering from a condition or symptoms of migraine is an amount of active ingredient from about, for example, 0.1 $\mu$g/kg to about 100 mg/kg body weight. For parenteral administration, the dose may be in the range of about 1 $\mu$g/kg to about 100 mg/kg body weight for intravenous administration. For oral administration, the compositions may be provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the individual to be treated. The active ingredient will preferably be administered either continuously, or in equal doses, for example, from one to four times per day. Usually a small dosage is administered and the dosage is gradually increased until the optimal dosage for the individual undergoing treatment is determined.

In addition, the dosage level will vary depending upon the bioavailability of the compound. The more bioavailable and potent the compound, the less amount of the compound will need to be administered through any delivery route, including, but not limited to, oral delivery. The dosages of the KCNQ potassium channel openers/activators are adjusted when combined in order to achieve desired effects. On the other hand, dosages of the opener/activator compounds may be independently optimized and combined to achieve a synergistic result wherein the pathology is reduced more than it would be if one single agent or compound were used alone.

It is to be understood that the amount of the compound actually administered will be determined by a physician in the light of the relevant circumstances, including the condition to be treated, the choice of compound to be administered, the selected route of administration, the mode of administration, the age, weight and response of the individual patient and the severity of the individual's symptoms and/or condition.

Another embodiment of the present invention provides methods for treating or preventing migraine or migraine headache, or diseases similar, or mechanistically related to migraine, in a mammal, preferably humans, in need thereof. Treatment includes reduction, amelioration, suppression, or alleviation of migraine pain and/or its associated symptoms and characteristics. The method and KCNQ opener compounds utilized therein may also be efficacious in the treatment or prevention of symptoms associated with migraine prior to a full-blown migraine attack, as well as in the treatment of active migraine or migraine headache after onset.

The method according to this invention comprises administering to an individual in need thereof an effective amount of a KCNQ opener compound according to the invention, non-limiting examples of which include compounds of Formula I or Formula II, or a pharmaceutically acceptable salt, solvate, or hydrate thereof, so as to treat (e.g., reduce, ameliorate, or eliminate) or prevent migraine pain, migraine symptoms, and/or other characteristics that are associated with a migraine attack. Preferred are the fluorooxindole compound, (+)-3-[5-Chloro-2-[(2,2,2-trifluoroethoxy)phenyl]-1,3-dihydro-3-fluoro-6-trifluoromethyl)-2H-indol-2-one, and the 2-(Pyrrolidin-1-yl)-4-(trifluoromethyl)-N-[[4-(trifluoromethyl)phenyl]methyl]pyrimidine-5-carboxamide compound, or a pharmaceutically acceptable salt, solvate, or hydrate thereof.

In another of its aspects, the present invention provides methods for screening and identifying drugs and/or biological compounds that interact with and/or modulate CNS KCNQ potassium channel proteins, particularly those drugs and compounds that function to open, preferably, selectively open, CNS KCNQ potassium channel proteins. Particularly useful are those drugs and compounds which are able to result in a CNS KCNQ potassium channel protein's ability to prevent the asynchronous firing of neurons as described herein; the so-identified drugs or agents can be used to effect the treatment of migraine, and other diseases that are similar, or mechanistically related to, migraine. Such methods employ CNS-associated KCNQ potassium channels for detecting those drugs and biological agents that interact with and/or open the CNS KCNQ channel proteins. In accordance with this invention, the so-identified drugs and biologic agents are tested, e.g., via trigeminal field potential analysis as described herein, to determine if their opener or activator function protects against abnormal synchronous neuronal firing associated with migraine. Other analyses for migraine treatment effectiveness that can be performed, if desired, include the attenuation of cortical spreading depression as described herein. Most preferably, the screening methods will detect and identify those drugs or biological agents that are openers or activators of the KCNQ potassium channel proteins, such as the CNS KCNQ2, KCNQ3, KCNQ4, KCNQ5, and heteromultimers thereof, and which function as therapeutics in the treatment of migraine.

The CNS KCNQ potassium channel polypeptides, or peptide portions or fragments thereof, can be used for screening libraries of compounds in any of a variety of drug screening techniques. The CNS KCNQ potassium channel protein employed in such screening may be free in solution, affixed to a solid support, borne on a cell surface, located intracellularly, or expressed in membranes via transfection or transformation. The formation of binding complexes between the CNS KCNQ polypeptide, or portion thereof, and the agent being tested, may be measured utilizing techniques commonly practiced in the art. The agents which bind can then be tested as described in Examples 3 and/or 4 herein.

One technique for drug screening which may be used provides for high throughput screening of compounds having suitable binding affinity to the protein of interest, such as described in WO 84/03564. In this method, as applied to KCNQ potassium channel proteins, large numbers of different small test compounds are synthesized on a solid substrate, such as plastic pins or some other surface. The test compounds are reacted with KCNQ potassium channel polypeptide, or fragments thereof, and washed. Bound CNS KCNQ potassium channel polypeptide is then detected by methods well known in the art. Those agents that are identified through the screening methods are assayed and evaluated for their ability to modulate CNS KCNQ potassium channel proteins, preferably to open the channels, employing methods as described herein, e.g., an oocyte expression assay, Example 4). In turn, the agents are further identified as agents to treat migraine, as described herein, e.g., in the in vivo electrophysiology studies described in Example 3.

Other screening and small molecule (e.g., drug) detection assays which involve the detection or identification of small molecules that can bind to a CNS KCNQ potassium channel protein, are encompassed by the present invention. Particularly preferred are assays suitable for high throughput screening methodologies. In such binding-based screening or detection assays, a functional assay is not typically required. However, a functional assay can be performed in conjunction with the binding assay, for example, after those molecules which bind to the CNS KCNQ potassium channel have been detected. For the assay, a target protein and a library or panel of compounds (e.g., ligands, drugs, small molecules) to be screened or assayed for binding to the protein target are employed. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, Gen. Eng. News, 20(8)). The assay allows the detection of small molecules (e.g., drugs, ligands) that bind to expressed CNS KCNQ potassium channel polypeptides based on affinity of binding determinations, for example, by analyzing thermal unfolding curves of protein-drug or ligand complexes. The drugs or binding molecules determined by this technique can be further assayed, if desired, by methods to determine if the molecules affect or modulate function or activity of the target protein, for example, if the molecules are openers or activators of the potassium channel polypeptides, using the assays described herein.

According to the present invention, the CNS KCNQ potassium channel proteins can be used, for example, as targets in screening assays of candidate bioactive agents that modulate CNS KCNQ potassium channel bioactivity, particularly, to identify those agents that specifically open or activate these channels and allow hyperpolerization of neurons, for treating migraine and its associated symptoms, and/or cluster headaches.

Activators or openers of CNS KCNQ potassium channels may be identified by screening compounds to ascertain their effects on opening these channels and allowing hyperpolerization in the trigeminovascular system. In an embodiment of the present invention, compounds are screened to identify activators by contacting an expressed CNS KCNQ polypeptide with a test compound, determining its activator or opener activity on the CNS KCNQ potassium channel. Such activator or opener compounds can then be evaluated in the superior sagittal sinus (SSS)-stimulated trigeminal field response assay compared with vehicle control. Preferably, a useful anti-migraine test compound according to this aspect of the invention causes significant reductions in SSS-stimulated trigeminal field potential amplitudes compared with vehicle. In addition, a useful anti-migraine test compound also causes attenuation of cortical spreading depression as described herein.

Test or candidate bioactive agents include specific antibodies, non-natural binding agents identified in screens of chemical libraries, peptide analogs, etc., particularly those having a low toxicity for human cells. The term "agent" as used herein generally describes any molecule, e.g., protein, oligopeptide, small organic molecule or chemical compound, drug, polysaccharide, polynucleotide, etc., having the capability of directly or indirectly activating or opening CNS KCNQ potassium channel.

By way of nonlimiting example, candidate agents encompass numerous chemical classes, though typically they are organic molecules, preferably small organic compounds having a molecular weight of more than 100 and less than about 10,000 daltons, preferably less than about 2000 to 5000 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. In addition, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

The determination of the binding of the candidate bioactive agent to a CNS KCNQ potassium channel polypeptide may be accomplished in a number of ways practiced in the art. In one aspect, the candidate bioactive agent is labeled, and binding is determined directly. Where the screening assay is a binding assay, one or more of the molecules may be joined to a label, where the label can directly or indirectly provide a detectable signal. Various labels include radioisotopes, fluorescent and chemiluminescent compounds, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule which allows detection, in accordance with known procedures. In some embodiments, only one of the components is labeled. Alternatively, more than one component may be labeled with different labels; for example, the CNS KCNQ polypeptide may be labeled with one fluorophor and the candidate agent labeled with another In one embodiment, the candidate bioactive agent is labeled. Labeled candidate bioactive agents are incubated with the KCNQ potassium channel polypeptide for a time sufficient to allow binding, if present. Incubations may be performed at any temperature which facilitates optimal activity, typically between 4° C. and 40° C. Incubation periods are selected for optimum activity, but may also be optimized to facilitate rapid high throughput screening. Typically between 0.1 and 1 hour is sufficient. Excess reagent is generally removed or washed away. The presence or absence of the labeled component is detected to determine and indicate binding.

In a preferred embodiment, the screening method comprises combining a CNS KCNQ protein, a candidate bioactive agent and determining whether the candidate agent opens the CNS KCNQ potassium channel by methods described herein (e.g., oocyte expression assay, Example 4), or by other suitable methods practiced in the art, and evaluating the performance of the selected opener compound(s) in the SSS-stimulated trigeminal field response assay.

Also encompassed by the present invention are the use of both native CNS KCNQ and variant CNS KCNQ potassium channel proteins and bioactive agents capable of modulating the bioactivity of one or both types of proteins. A differential screening method is contemplated to identify drug candidates that bind to, interact with, or open, for example, native CNS KCNQ potassium channel proteins, compared with binding, interaction or opener activity for variant CNS KCNQ potassium channel proteins, or modified CNS KCNQ potassium channel proteins. It is to be appreciated that, in some instances, variant CNS KCNQ potassium channel proteins can have modifications which allow these channels to perform, e.g., to reduce or prevent asynchronous firing of neurons, in a manner that is superior to the non-variant or unmodified form of the CNS KCNQ protein.

Preferably in such methods, all control and test samples are performed in at least triplicate to obtain statistically significant results. A variety of other reagents may be included in the screening assays/methods. Such reagents include, but are not limited to, salts, neutral proteins, e.g. albumin, detergents, etc., which may be used to facilitate optimal protein-protein binding and/or reduce non-specific or background interactions. In addition, reagents that otherwise improve the efficiency of the assay, such as protease inhibitors, nuclease inhibitors, anti-microbial agents, etc. may be used. Further, the mixture of components in the method may be added in any order that provides for the requisite binding or activity to be determined.

Kits are included as an aspect of the present invention which comprise containers with reagents necessary to screen test compounds, using, for example, expressed or purified CNS KCNQ potassium channel proteins and other ingredients for carrying out the screening assay, as well as instructions for performing the assay. Kits may optionally contain positive and/or negative controls.

EXAMPLES

The following examples as set forth herein are meant to illustrate and exemplify the various aspects of carrying out the present invention and are not intended to limit the invention in any way, inasmuch as many variations of the invention are possible within the spirit of the invention.

Example 1

Fluorooxindole KCNQ Opener Compound Synthesis/Preparation

In this Example, as in Example 2, all temperatures are given in degrees Centigrade. Melting points were recorded on a Gallenkamp capillary melting point apparatus; temperatures are uncorrected. Proton magnetic resonance ($^1$H NMR) was recorded on a Bruker AC 300. All spectra were determined in the solvents indicated and chemical shifts are reported in δ units downfield from the internal standard, tetramethylsilane (TMS), and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dq, doublet of quartet. Infrared (IR) spectra using potassium bromide (KBr) were determined on a Perkin Elmer 781 spectrophotometer from 4000 cm$^{-1}$ to 400 cm$^{-1}$, calibrated to 1601 cm$^{-1}$ absorption of a polystyrene film and reported in reciprocal centimeters (cm$^{-1}$). Low resolution mass spectra (MS) and the apparent molecular (MH$^+$) or (M–H)$^-$ was determined on a Finnigen TSQ 7000. High resolution mass spectra were determined on a Kratos MS50 in FAB mode using cesium iodide/glycerol as internal reference. The element analyses are reported as percent by weight.

It will be evident to the skilled practitioner that appropriate substitution of both the materials and the methods disclosed in this Example will produce the products illustrated below, as well as those embraced by the scope of the present invention.

Preparation of the 3-phenyl fluorooxindole compound (+)-3-[5-chloro-2-[(2,2,2-trifluoroethoxy)phenyl]-1,3-dihydro-3-fluoro-6-(trifluoromethyl)-2H-indol-2-one The following steps illustrate the procedure for the preparation of the 3-fluoro oxindole derivative, (+)-3-[5-chloro-2-[(2,2,2-trifluoroethoxy)phenyl]-1,3-dihydro-3-fluoro-6-(trifluoromethyl)-2H-indol-2one, as used in Example 3, according to the present invention.

1. Preparation of (±)-3-[5-Chloro-2-[(2,2,2-trifluoroethoxy)-phenyl]-1,3-dihydro-3-hydroxy-6-(trifluoromethyl)-2H-indol-2one Step A: Dibromoethane (0.77 mL) was added under nitrogen to a stirred suspension of magnesium turnings in dry THF (30 mL) and was allowed to react for 10–15 minutes. Neat 2-bromo-4-chloro(2,2,2-trifluoroethoxy) benzene (13.0 g, 45 mmol) was then added. Once the ensuing exothermic reaction had subsided, the reaction mixture was heated to reflux for 2–3 hours then was allowed to cool to room temperature.

Step B: In a separate flask, neat 6-(trifluoromethyl)isatin (6.45 g, 30 mmol) was added to a cold (0° C.) suspension of oil free NaH (60% in oil, 1.44 g, 36 mmol) in dry THF (30 mL) under nitrogen. The mixture was stirred until gas evolution ceased. The sodium salt of the 6-(trifluoromethyl) isatin was cooled to −20° C. and then the Grignard reagent 2-(magnesium bromide)-4-chloro(2,2,2-trifluoroethoxy) benzene (from Step A, above) was added via syringe. The reaction mixture was allowed to warm to room temperature and was maintained at room temperature for 30 minutes. The reaction mixture was diluted with diethyl ether and then quenched with 1N HCl. The organic layer was separated and washed consecutively with 0.5N NaOH (2×50 mL), 1N HCl, water, brine and then was dried over $Na_2SO_4$ and filtered. The filtrate was concentrated in vacuo to provide a light brown solid (16.3 g) which was triturated with $CH_2Cl_2$ to afford the compound (±)-3-[5-Chloro-2-[(2,2,2-trifluoroethoxy)phenyl]-1,3-dihydro-3-hydroxy-6-(trifluoromethyl)-2H-indol-2-one (8.92 g, 70%) as a white solid: mp 226–228° C.

2. Preparation of (±)-3-[5-chloro-2-[(2,2,2-trifluoroethoxy) phenyl]-1,3-dihydro-3-fluoro-6-(trifluoromethyl)-2H-indol-2-one Step C: Neat diethylaminosulfur trifluoride (3.66 mL, 0.03 mol) was added dropwise to a cold (−78° C.) stirred partial solution of (±)-3-[5-chloro-2-[(2,2,2-trifluoroethoxy) phenyl]-1,3-dihydro-3-hydroxy-6-(trifluoromethyl)-2H-indol-2-one (See, Steps A and B above; 6.4 g, 0.015 mol) in anhydrous $CH_2Cl_2$ (45 mL) under a nitrogen atmosphere. The resultant mixture was allowed to warm in an ice-bath and maintained at 0° C. After 1 hour, TLC showed absence of starting material. The reaction mixture was quenched with slow addition of cold water (20–25 mL) at 0° C. The organic layer was separated, washed with water (30 mL), brine (30 mL) and then dried over $MgSO_4$ and filtered. The filtrate was concentrated in vacuo to give the crude product (6.9 g). The crude product was purified by recrystallization from $CH_2Cl_2$/ether/hexanes to provide the titled compound as an off-white crystalline solid (5.94 g, 93%): mp 208–210° C.; $^1H$ NMR (DMSO-$d_6$): δ 4.50–4.65 (m, 2H), 7.12 (m, 2H), 7.30–7.35 (m, 2H), 7.56 (dd, 1H, J=5.3 and 1.6 Hz), 7.72 (d, 1H, J=1.4 Hz), 11.20 (s, 1H).

Anal. Calcd. for $Cl_7H_9ClF_7NO_2$: C, 47.74; H, 2.12, N, 3.27. Found: C, 47.63; H, 2.18, N, 3.21.

3. Isolation of (+)-3-[5-Chloro-2-[(2,2,2-trifluoroethoxy) phenyl]-1,3-dihydro-3-fluoro-6-(trifluoromethyl)-2H-indol-2-one (Compound 1)

Step D: The racemic compound (±)-3-[5-chloro-2-[(2,2,2-trifluoroethoxy)phenyl]-1,3-dihydro-3-fluoro-6-(trifluoromethyl)-2H-indol-2-one obtained in Step C above was separated into its enantiomers using a Chiracel-OD analytical HPLC column (250×4 mm) using 9:1 hexanes/isopropyl alcohol as the eluting solvent at a flow rate of 0.7 mL/min. The detection method employed an HP 1090 UV detector with diode array at a wavelength of 220 nm. The first enantiomer which eluted from the column had a retention time of about 8.64 minutes and was determined to be the (+)-enantiomer of the title compound. On a preparative scale, up to two grams of the racemate may be resolved with a single injection on a 5×50 cm Chiracel-OD preparative HPLC column using 9:1 hexanes/isopropyl alcohol at a flow rate of 60 mL/min with baseline separation. The (+)-enantiomer was identical to the racemate with respect to NMR, mass spectra, TLC and IR. The title compound was found to have a mp=68° C.–69° C. and $[\alpha]_D^{25}$+120.5° ($CHCl_3$).

Example 2

2-(Pyrrolidin-1-yl)-4-(trifluoromethyl)-N-[[4-(trifluoromethyl)phenyl]methyl]pyrimidine-5-carboxamide KCNQ Opener Compound Synthesis/Preparation Preparation of 2-(Pyrrolidin-1-yl)-4-(trifluoromethyl)-N-[[4-(trifluoromethyl)phenyl]methyl]pyrimidine-5-carboxamide (Compound 2)

To a solution of 2-chloro-4-(trifluoromethyl)pyrimidine-5-carbonyl chloride (0.74 g, 3.0 mmol) in dichloromethane (5 mL), was added saturated sodium bicarbonate (5 mL) and 4-(trifluoromethyl)benzylamine (0.58 g, 3.3 mmol). The reaction mixture was stirred at room temperature for 3 hours. The precipitated white solid of 2-chloro-4-(trifluoromethyl)-N-[[4-(trifluoromethyl)phenyl]methyl]pyrimidine-5-carboxamide was collected by filtration and then dissolved in acetonitrile (10–15 mL). Potassium carbonate (0.62 g, 4.5 mmol) and pyrrolidine (0.43 g, 6 mmol)) were added. The reaction mixture was stirred at room temperature overnight. The inorganic salts were filtered off and the filtrate was concentrated in vacuo to provide the pure titled compound: MS m/e 419 (MH$^+$). $^1H$ NMR (DMSO-$d_6$): δ 9.10 (t, J=5.9 Hz, 1H), 8.68 (s, 1H), 7.71 (d, J=8.1 Hz, 2H), 7.55 (d, J=8.0 Hz, 2H), 4.51 (d, J=6.1 Hz, 2H), 3.5–3.55 (m, br, 4H), 1.93–1.98 (m, 4H).

Example 3

In vivo Electrophysiology

Materials and Methods

Male Long-Evans rats (Harlan, 250–400 g) were used in the experiments described in this example. Prior to testing, rats were allowed access to food and water ad libitum and were maintained on a 12:12 hours light/dark cycle. Rats were group housed in an Association for Assessment and Accreditation of Laboratory Animal Care (A.A.A.L.A.C.) accredited facility and cared for in strict compliance with all applicable regulations.

Cortical Spreading Depression

Rats were anesthetized with urethane anesthesia (1.2 g/kg i.p.), implanted with a jugular vein catheter for drug injections, and placed in a stereotaxic frame. The skull was exposed and a small hole (approximately 2 mm by 3 mm) was drilled in the skull rostral to the lambdoid suture using a microdrill and steel burr creating a "well". The dura was disrupted and a drop of mineral oil was placed in this well.

Crystalline KCl was later applied to the well for 10 minutes to elicit spreading depression. Typically, this application produced a long-lasting series of spreading depressions.

Two additional holes were placed in the skull unilaterally at 4 and 8 mm rostral to the application hole. Silver wire electrodes were placed in these latter holes and secured to the skull using acrylic cement. These electrodes were used to record DC deflections following application of KCl. A similar silver wire electrode, sutured to the nuchal muscle, served as a reference electrode. Electrical DC recordings were made using a standard amplifier (Warner, DP-304) and commercially available data acquisition equipment (Cambridge Electronic Design, 1401 A-D converter and Spike2 software). The number of spreading depressions produced by the 10 minute application of KCl was the primary measure used to access the effectiveness of compounds.

Differences between control and drug conditions were assessed using analyses of variance (ANOVA) and appropriate post-hoc analyses. The Mann-Whitney U non-parametric test was utilized when unequal variances were encountered. A difference was considered significant when $p \leq 0.05$.

SSS Stimulation and Recording

SSS stimulation and recording were performed in a manner consistent with previously published methods using cat (K. L. Hoskin et al., 1996, Brain, 119:101–108) and rat (M. J. Cumberbatch et al., 1998, Eur. J. Pharmacol., 362:43–46; and M. J. Cumberbatch et al., 1999, Br. J. Pharmacol., 126:1478–1486) animal models. Rats were anesthetized with 1.2 g/kg i.p. urethane (#U-2500, Sigma Chemical Company, St. Louis, Mo.) and given supplemental urethane as needed. In the case of intravenous (i.v.) drug administration (e.g., (+)-3-[5-Chloro-2-[(2,2,2-trifluoroethoxy)phenyl]-1,3-dihydro-3-fluoro-6-(trifluoromethyl)-2H-indol-2-one), the jugular veins of the rats were cannulated using sylastic tubing pre-filled with vehicle.

Rats were placed in a stereotaxic device (#1730, David Kopf Instruments, Tujunga, Calif.) and an incision was made to expose the entire skull that continued caudally to the level of the C1/C2 vertebral juncture. Using a microdrill (#770, Dremel, Racine, Wis.) and #4 carbide burr (Henry Schein, Melville, N.Y.), a square section of skull was removed extending from the bregma position, rostrally, to the lambda position, caudally. The underlying dura mater was incised bilateral to the SSS and a small section of Parafilm® (American National Can, Neenah, Wis.) was placed under the SSS to isolate the stimulation electrode. The SSS was stimulated using insulated silver electrodes bent at their ends to form a hook. The dorsal region of the vertebra corresponding to C2 was removed for access to the trigeminal nucleus caudalis.

Stimulated field responses were recorded in the trigeminal nucleus caudalis using Teflon coated stainless-steel microelectrodes (5 MΩ impedance, Frederick Haer, Brunswick, Me.) and amplified and filtered (0.1 Hz–10 kHz) using a differential amplifier (#IsoDAM8, World Precision Instruments, Sarasota, Fla.). Stimulation voltage (250 μsec, 40–130V) was delivered using a Grass S88 (Grass Medical Instruments, Quincy, Mass.) stimulator and stimulus isolation unit (Grass #SIU5) at a rate of 0.3 Hz. Amplified potentials were captured with an analog-to-digital converter (#1401 plus, Cambridge Electronic Design, Cambridge, UK) and commercially available software (#Signal, Cambridge Electronic Design). Low temperature wax was applied to both the recording and stimulation sites to prevent dehydration.

Three baseline measures (i.e., 100% of control), each consisting of 100 evoked trigeminal field potentials, were sampled prior to drug injection. The primary measure for efficacy were changes in trigeminal field potential amplitude following injection of test compound. A decrease in trigeminal field response amplitude was considered to evidence anti-migraine activity. Following injection of test substances, data were sampled for 1 hour, averaged into 5 minute bins (90 evoked potentials) and expressed as a percent change from average baseline values for the purposes of statistical analysis. Data were analyzed using repeated measures analyses of variance comparing vehicle and drug effects. A difference was considered significant when $p<0.05$.

Results

The three KCNQ channel openers examined in these studies, namely, the fluorooxindole compound (+)-3-[5-Chloro-2-[(2,2,2-trifluoroethoxy)phenyl]-1,3-dihydro-3-fluoro-6-(trifluoromethyl)-2H-indol-2-one, the 2-(Pyrrolidin-1-yl)-4-(trifluoromethyl)-N-[[4-(trifluoromethyl)phenyl]methyl]pyrimidine-5-carboxamide compound, and retigabine were prepared as a solution in 100% polyethylene glycol (MW=400) using sonication to aid in dissolution. The (+)-3-[5-Chloro-2-[(2,2,2-trifluoroethoxy)phenyl]-1,3-dihydro-3-fluoro-6-(trifluoromethyl)-2H-indol-2-one compound and the 2-(Pyrrolidin-1-yl)-4-(trifluoromethyl)-N-[[4-(trifluoromethyl)phenyl]methyl]pyrimidine-5-carboxamide compound were administered via the i.v. catheters described above at a maximum volume of 0.3 cc. Retigabine was administered by intraperitoneal (i.p.) injection at volume of 1 cc/kg.

As depicted in FIG. 1, the fluorooxindole compound, (+)-3-[5-Chloro-2-[(2,2,2-trifluoroethoxy)phenyl]-1,3-dihydro-3-fluoro-6-(trifluoromethyl)-2H-indol-2-one (Compound 1) produced a dose-dependent reduction in the SSS-stimulated trigeminal field response (overall ANOVA, $p<0.001$). Significant reductions compared with vehicle were observed following the use of doses 0.1, 1.0, 10.0, 30.0 and 50.0 mg/kg i.v. , ($p<0.01$ in all cases).

Figure 2:
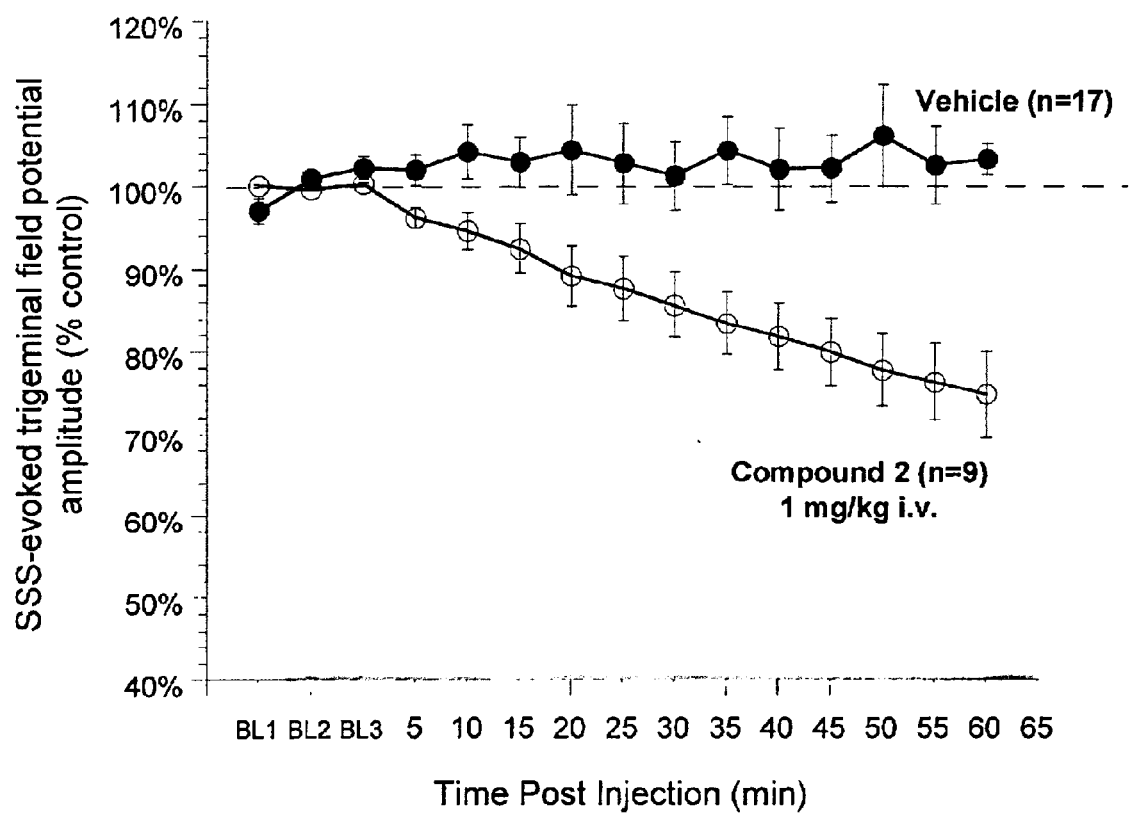
FIG. 2 shows effect of the 2,4-disubstituted pyrimidine-5-carboxamide derivative compound, 2-(Pyrrolidin-1-yl)-4-(trifluoromethyl)-N-[[4-(trifluoromethyl)phenyl]methyl]pyrimidine-5-carboxamide, (Compound 2), (1 mg/kg i.v.) on superior sagittal sinus (SSS) stimulation evoked trigeminal field potential amplitude in urethane anesthetized rats. BL1–BL3 each represent the average of 100 baseline recordings. This compound produced a statistically significant (p=0.005) decrease in field potential amplitude consistent with an anti-migraine profile for this compound. Error bars represent the stand error of the mean.

FIG. 2 shows that the 2-(Pyrrolidin-1-yl)-4-(trifluoromethyl)-N-[[4-(trifluoromethyl)phenyl]methyl]pyrimidine-5-carboxamide (Compound 2) produced a statistically significant ($p=0.005$) decrease in the SSS-stimulation-evoked trigeminal field potential amplitude, consistent with an anti-migraine profile for this compound.

Figure 3:
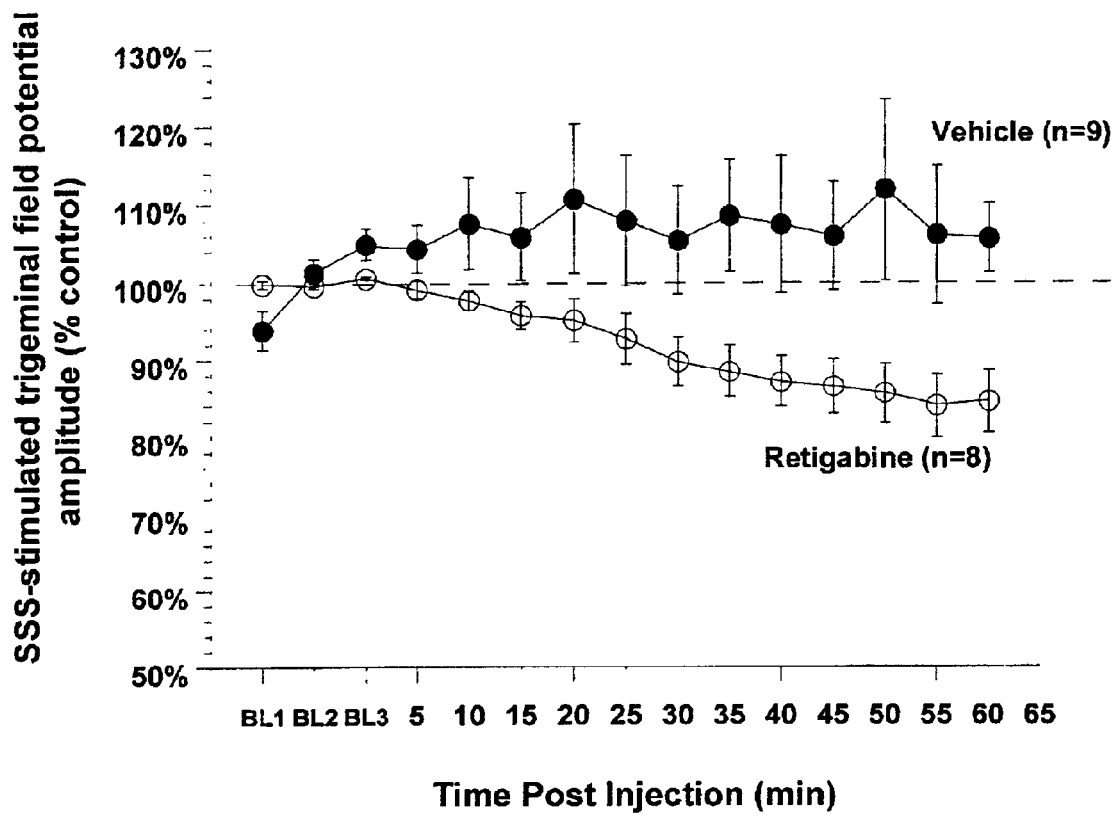
FIG. 3 depicts the effect of the potassium channel opener retigabine on SSS-stimulated field responses recorded in the nucleus trigeminal caudalis. This compound (3 mg/kg i.p.) produced a significant reduction in field response. (See Example 3). Error bars signify standard error of the mean (SEM).

FIG. 3 demonstrates that retigabine (3 mg/kg i.p.) was able to produce a significant reduction in SSS-stimulated trigeminal field potential amplitudes ($p<0.05$).

Figure 7:
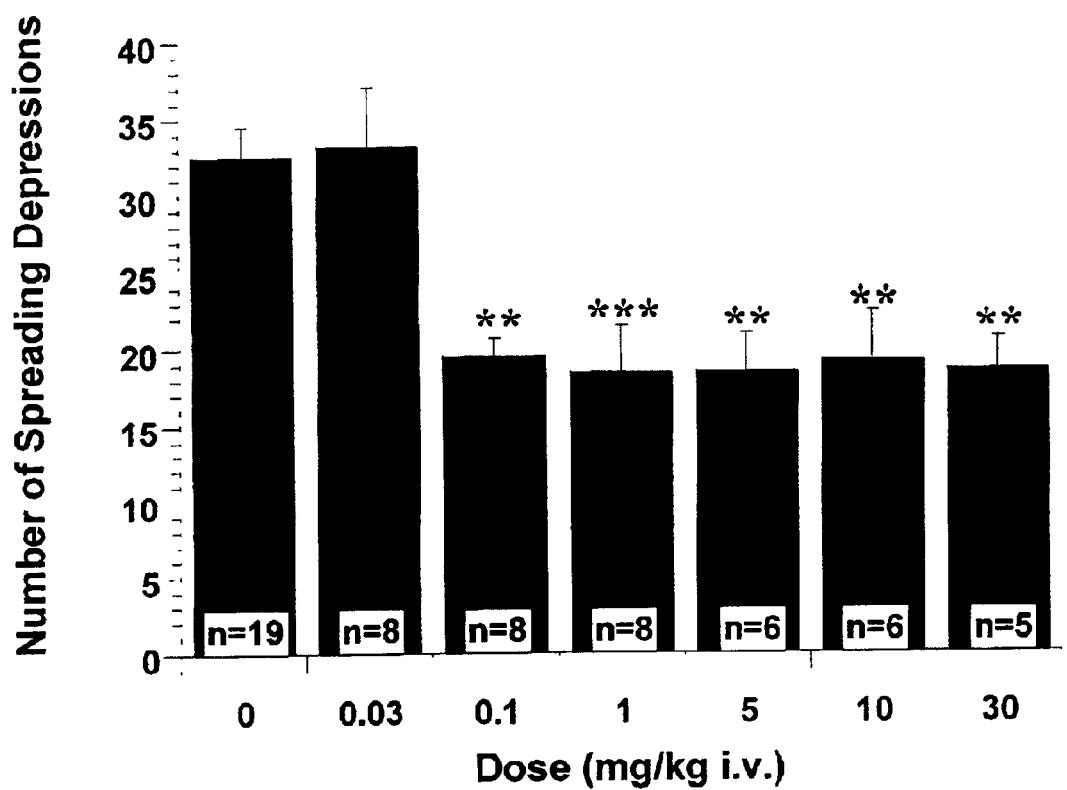
FIG. 7 demonstrates that the fluorooxindole derivative (+)-3-[5-Chloro-2-[(2,2,2-trifluoroethoxy)phenyl]-1,3-dihydro-3-fluoro-6-(trifluoromethyl)-2H-indol-2-one, (Compound 1), produced a significant reduction in the number of spreading depressions produced by a single 10 minute KCl application (overall ANOVA, F(6,54)=7.748, p<0.001) at various doses in the cortical spreading depression experiment described in Example 3.

In addition, as depicted in FIG. 7, the fluorooxindole derivative (+)-3-[5-Chloro-2-[(2,2,2-trifluoroethoxy)phenyl]-1,3-dihydro-3-fluoro-6-(trifluoromethyl)-2H-indol-2-one (Compound 1) produced a significant reduction in the number of spreading depressions produced by a single 10 min KCl application (overall ANOVA, $F(6,54)=7.748$, $p<0.001$) at various doses. Post-hoc comparisons using the Dunnett test (two-sided) revealed significant reductions compared with vehicle at doses of 0.1 ($p=0.002$), 1.0 ($p<0.001$), 5.0 ($p=0.002$), 10.0 ($p=0.004$), and 30.0 ($p=0.005$) mg/kg i.v., but not at the 0.03 mg/kg dose. With the exception of the 0.1 mg/kg dose ($F(7,18)=0.172$, $p<0.014$), all other doses were compliant with the underlying assumption of homogeneity of variance for these parametric analyses. Non-parametric analysis comparing vehicle and 0.1 mg/kg (+)-3-[5-Chloro-2-[(2,2,2-trifluoroethoxy)phenyl]-1,3-dihydro-3-fluoro-6-(trifluoromethyl)-2H-indol-2-one confirmed the difference found in the parametric analysis (Mann-Whitney U test statistic=10, $p<0.001$).

The results described above for the in vivo SSS-field potential experiments demonstrate that the novel fluorooxindole and 2,4-disubstituted pyrimidine-5-carboxamide derivative compounds are useful for modulating neuronal activity and can result in protection from abnormal synchronous firing during a migraine attack. Accordingly, the KCNQ opener or activator compounds described according to the present invention are capable of selectively limiting neuronal activity within the trigeminovascular system, and are thus particularly useful for the treatment of migraine headache and migraine attack in individuals suffering from the pain and discomfort of migraine and mechanistically similar or related diseases.

Example 4

Evaluation of KCNQ Modulation in Oocytes

The KCNQ family of potassium channel proteins exemplified by KCNQ2, KCNQ2/3 heteromultimers, and KCNQ5, is regulated by transmembrane voltage and plays a potentially important role in the regulation of neuronal excitability (C. Biervert et al., 1998, *Science*, 279: 403–406; C. Lerche et al., 2000, *J. Biol. Chem.*, 275:22395–22400; and H. Wang et al., 1998, *Science*, 282:1890–1893).

An opener of KCNQ channels, such as the KCNQ2 and KCNQ2/3 channel opener retigabine, exerts its cellular effects by increasing the open probability of these channels (J. Main, 2000, *Mol. Pharmacol.*, 58(2):253–62; A. Wickenden et al., 2000, *Mol. Pharm.*, 58:591–600). This increase in the opening of individual KCNQ channels collectively results in the hyperpolarization of cell membranes, particularly in depolarized cells, produced by significant increases in whole-cell KCNQ-mediated conductance.

The ability of the compounds described herein to open KCNQ channels and increase whole-cell outward ($K^+$) KCNQ-mediated currents was assessed under voltage-clamp conditions by determining their ability to increase cloned human mouse KCNQ2 (mKCNQ2)-mediated, heteromultimeric murine KCNQ2/3 (mKCNQ2/3)-mediated, and heterologous human KCNQ5 (hKCNQ5)-mediated outward currents expressed in *Xenopus* oocytes. Oocytes were prepared and injected using standard techniques; each oocyte was injected with approximately 50 nl of mKCNQ2, or hKCNQ5 cRNA. In the case of mKCNQ2/3 heteromultimeric channel expression, equal amounts (25–50 nL) of each cRNA were co-injected. Injection of equivalent amounts of water (50 nl) did not result in expression of outward currents at the voltage steps used to detect KCNQ expression.

Following injection, oocytes were maintained at 17° C. in ND96 medium containing (in mM): NaCl, 90; KCl, 1.0; $CaCl_2$, 1.0; $MgCl_2$, 1.0; HEPES, 5.0; pH 7.5. Horse serum (5%) and penicillin/streptomycin (5%) were added to the incubation medium. Recording commenced 2–6 days following mRNA injection. Prior to the start of an experiment, oocytes were placed in a recording chamber and incubated in Modified Barth's Solution (MBS) containing (in mM): NaCl, 88; $NaHCO_3$, 2.4; KCl, 1.0; HEPES, 10; $MgSO_4$, 0.82; $Ca(NO_3)_2$, 0.33; $CaCl_2$, 0.41; pH 7.5.

Frog (*Xenopus laevis*) oocytes were impaled with electrodes (1–2 MΩ) and standard 2-electrode voltage clamp techniques were employed to record whole-cell membrane currents. Recordings were achieved using standard two-electrode voltage clamp techniques (e.g., W. Stuhmer et al., 1992, *Methods in Enzymology*, 207:319–339). Voltage-clamp protocols typically comprised a series of voltage steps of 1–5 seconds duration, in +10 mV steps from a holding potential of −90 mV to a maximal potential of +40 mV. Records were digitized at 5 kHz and stored on a computer using pClamp data acquisition and analysis software (Axon Instruments). Compounds were evaluated at a single concentration (10 or 20 µM), and the effect of the selected compounds of Formula I on KCNQ2 current was expressed as the percent of control current. For the Formula I compound, (+)-3-[5-Chloro-2-[(2,2,2-trifluoroethoxy)phenyl]-1,3-dihydro-3-fluoro-6-(trifluoromethyl)-2H-indol-2-one, 10 µM of this 3-phenyl oxindole derivative increased the KCNQ2 current>150% over the KCNQ2 current in controls.

Figure 4:
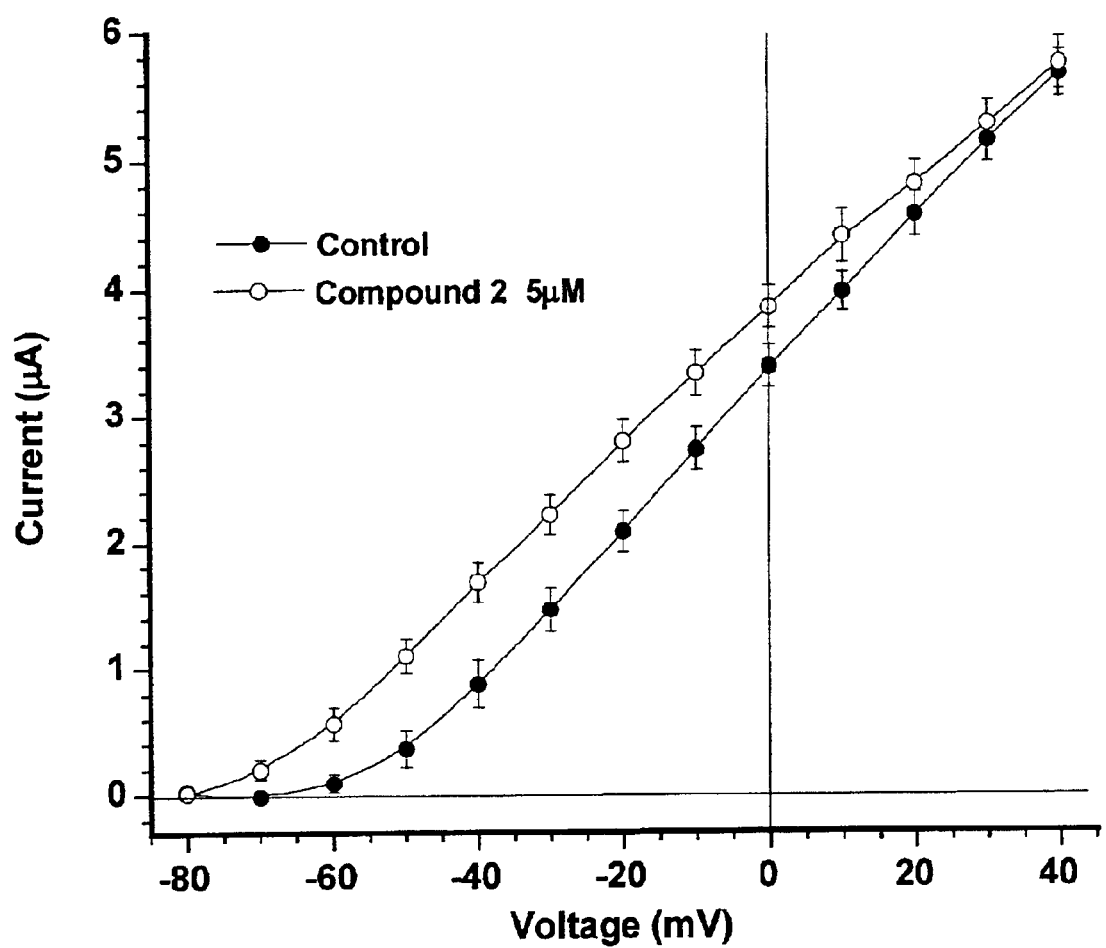
FIG. 4 shows the effects of 2-(Pyrrolidin-1-yl)-4-(trifluoromethyl)-N-[[4-(trifluoromethyl)phenyl]methyl]pyrimidine-5-carboxamide, (Compound 2), on *Xenopus* oocyte expressed murine KCNQ2-mediated outward currents. (See Example 4).
Figure 5:
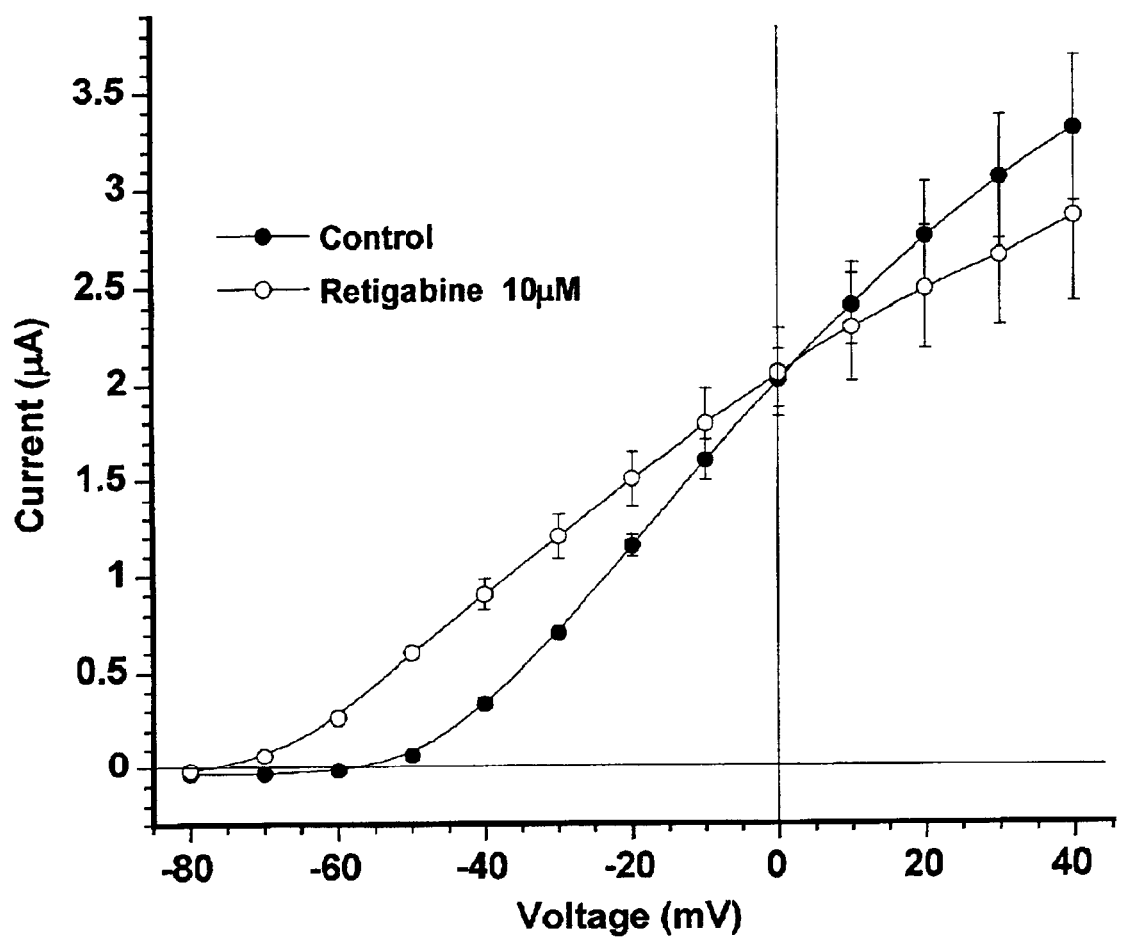
FIG. 5 shows the effects of retigabine (10 µM) on *Xenopus* oocyte expressed murine KCNQ2-mediated outward currents. (See Example 4).
Figure 6:
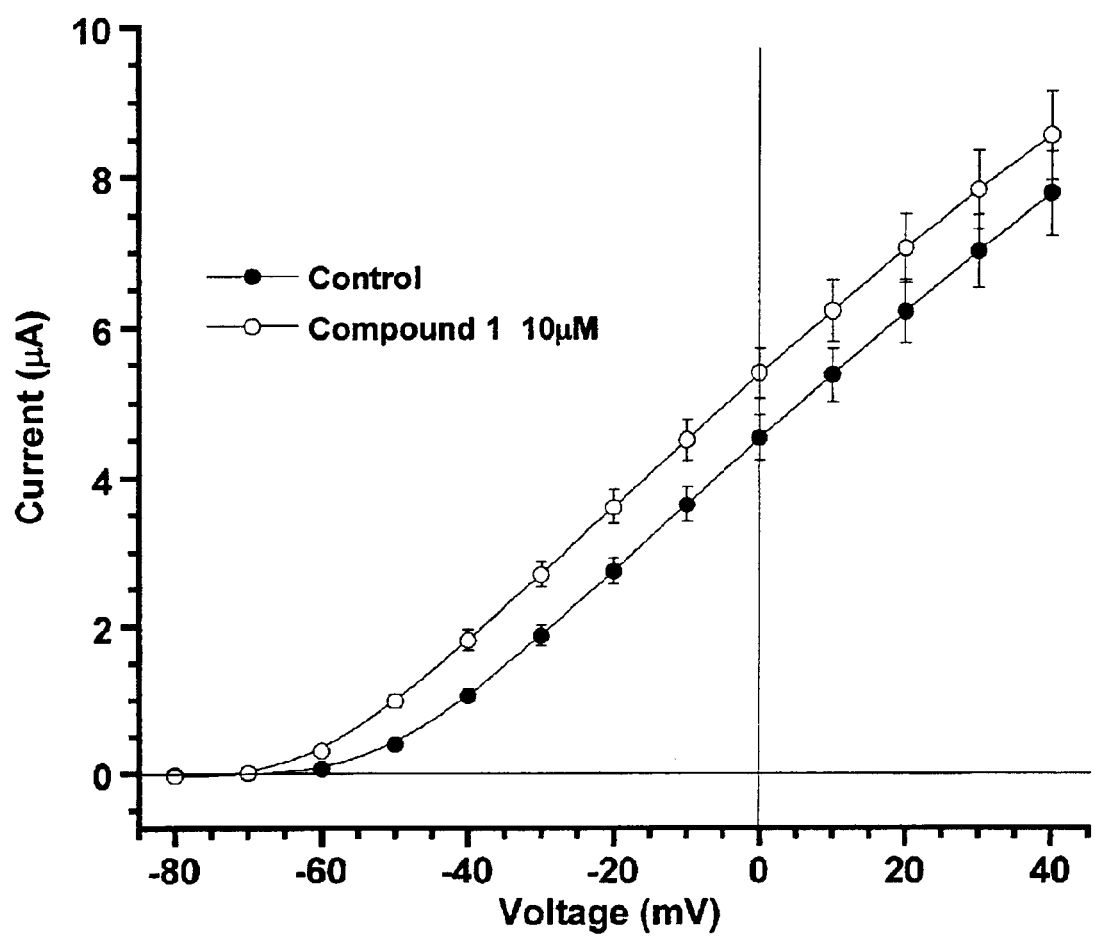
FIG. 6 shows the effects of the compound (+)-3-[5-Chloro-2-[(2,2,2-trifluoroethoxy)phenyl]-1,3-dihydro-3-fluoro-6-(trifluoromethyl)-2H-indol-2-one on *Xenopus* oocyte-expressed murine KCNQ2-mediated outward currents. (See Example 4).

The effects of 2-(Pyrrolidin-1-yl)-4-(trifluoromethyl)-N-[[4-(trifluoromethyl)phenyl]methyl]pyrimidine-5-carboxamide on *Xenopus* oocyte expressed murine KCNQ2 (mKCNQ2)-mediated outward currents are shown in FIG. 4. The effects of retigabine (10 µM) on *Xenopus* oocyte expressed mKCNQ2-mediated outward currents are shown in FIG. 5. The effects of (+)-3-[5-Chloro-2-[(2,2,2-trifluoroethoxy)phenyl]-1,3-dihydro-3-fluoro-6-(trifluoromethyl)-2H-indol-2-one on *Xenopus* oocyte-expressed mKCNQ2-mediated outward currents are shown in FIG. 6. In addition, the effect of (+)-3-[5-Chloro-2-[(2,2,2-trifluoroethoxy)phenyl]-1,3-dihydro-3-fluoro-6-(trifluoromethyl)-2H-indol-2-one on *Xenopus* oocyte-expressed human KCNQ5-mediated outward currents was 157.4+/−6.0% of control (n=3).

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. An opener or activator compound which modulates the biological activity of central nervous system-associated KCNQ potassium channel polypeptides by hyperpolarizing neurons that fire before or during a migraine headache or migraine-related disorder, the opener or activator compound comprising a compound according to Formula I and pharmaceutically acceptable salts thereof, Formula I having the structure

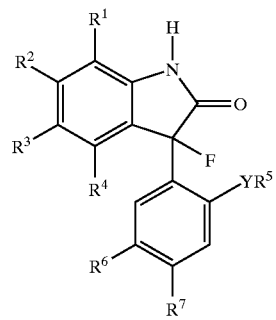

wherein
   $R^1$, $R^2$, $R^3$ and $R^4$ are each independently hydrogen, $C_{1-4}$ alkyl halogen, fluoromethyl, trifluoromethyl, phenyl, 4-methylphenyl or 4-trifluromethylphenyl;

$R^5$ is $C_{1-6}$ alkyl, optionally substituted with one to three same or different groups selected from fluoro and chloro, provided that $R^5$ is not $C_{1-6}$ alkyl when Y is O;

Y is O or S; and $R^6$ and $R^7$ are each independently hydrogen, chloro, bromo or trifluoromethyl.

2. The compound according to claim 1, wherein the opener or activator compound is (+)-3-[5-Chloro-2-[(2,2,2-trifluoroethoxy)phenyl]-1,3-dihydro-3-fluoro-6-(trifluoromethyl)-2H-indol-2-one.

3. The compound according to claim 1, wherein the KCNQ potassium channel polypeptide is selected from the group consisting of one or more of KCNQ2, KCNQ3, KCNQ4, KCNQ5, and heteromultimers thereof.

4. A method of modulating neuronal activity associated with migraine or a migraine-related disorder, comprising administering to an individual in need thereof an amount of the compound according to claim 1 effective to inhibit neuronal activity, thereby reducing, ameliorating or alleviating migraine or a migraine-related disorder.

5. The method according to claim 4, wherein said neuronal activity is selectively inhibited with the trigeminovascular system of the central nervous system.

6. A method of treating migraine or migraine-related disorder, comprising: administering to an individual in need thereof an opener of a CNS-located KCNQ potassium channel protein, or functional portion thereof, according to claim 1, in an amount effective to selectively limit neuronal hyperexcitablility during a migraine attack or migraine-related disorder by opening the CNS-located KCNQ potassium channel protein so as to protect against abnormal synchronous firing of neurons.

7. The method according to claim 6, wherein the neuronal hyperexcitability occurs within the trigeminovascular system of the central nervous system.

8. The method according to claim 4 or claim 6, wherein the KCNQ potassium channel protein is selected from the group consisting of KCNQ2, KCNQ3, KCNQ4, KCNQ5 and heteromultimers thereof.

* * * * *